(12) United States Patent
Carmon

(10) Patent No.: US 9,642,903 B2
(45) Date of Patent: May 9, 2017

(54) ANTIGEN SPECIFIC MULTI EPITOPE-BASED ANTI-INFECTIVE VACCINES

(75) Inventor: Lior Carmon, Tel Aviv (IL)

(73) Assignees: LIOR CARMON, Tel-Aviv (IL); VAXIL BIOTHERAPEUTICS LTD., Nes-Ziona (IL)

( * ) Notice: Subject to any disclaimer, the term of this patent is extended or adjusted under 35 U.S.C. 154(b) by 0 days.

(21) Appl. No.: 13/384,286

(22) PCT Filed: Jul. 15, 2010

(86) PCT No.: PCT/IL2010/000569
§ 371 (c)(1),
(2), (4) Date: Jan. 16, 2012

(87) PCT Pub. No.: WO2011/007359
PCT Pub. Date: Jan. 20, 2011

(65) Prior Publication Data
US 2012/0177677 A1 Jul. 12, 2012

Related U.S. Application Data

(60) Provisional application No. 61/225,957, filed on Jul. 16, 2009.

(51) Int. Cl.
| | | |
|---|---|---|
| A61K 39/12 | (2006.01) | |
| A61K 39/00 | (2006.01) | |
| A61K 31/04 | (2006.01) | |
| A61K 39/09 | (2006.01) | |
| A61P 37/04 | (2006.01) | |
| A61K 39/04 | (2006.01) | |

(52) U.S. Cl.
CPC ...... *A61K 39/04* (2013.01); *A61K 2039/6031* (2013.01); *A61K 2039/6068* (2013.01); *A61K 2039/6075* (2013.01)

(58) Field of Classification Search
CPC .... A61K 2039/6031; A61K 2039/6068; A61K 2039/6075; A61K 39/04
USPC ......................................................... 424/188
See application file for complete search history.

(56) References Cited

U.S. PATENT DOCUMENTS 5,846,827 A * 12/1998 Celis .................... C12N 5/0636
424/93.1
2004/0197896 A1* 10/2004 Cole .......................... 435/252.3

FOREIGN PATENT DOCUMENTS

| EP | 0 519 218 A2 | 12/1992 |
|---|---|---|
| WO | WO0006723 * | 2/2000 |
| WO | 02074903 A3 | 9/2002 |
| WO | 2008/035350 A1 | 3/2008 |
| WO | WO2008035350 * | 3/2008 |
| WO | WO2008043180 * | 4/2008 |

OTHER PUBLICATIONS

Martolio et al., Signal sequences: more than just greasy peptides, 1998, Trends in Cell Biology, 8:410-415.*
Mollay et al., "Cleavage of honeybee prepromelittin by an endoprotease from rat liver microsomes: identification of intact signal peptide", 1982, Proc. Natl. Acad. Sci. USA, 79:2260-2263.*
Kim et al., "Peptide amidation: production of peptide hormones in vivo and in vitro", 2001, Biotechnol. Bioprocess Eng., 6:244-251.*
Small et al. GenBank:EFD49411.1, The Broad Institute Genome Sequencing Platform, Direct Submission, Jun. 2008: pdf 1 page.*
Small2 et al., GenBank:EFD79015.1 and EFD61432, The Broad Institute Genome Sequencing Platform, Direct Submission, May 2008: pdf 4 pages.*
Andersen, "Effective Vaccination of Mice against *Mycobacterium tuberculosis* Infection with a Soluble Mixture of Secreted Mycobacterial Proteins", Infection and Immunity, vol. 62, No. 6, pp. 2536-2544, (1994).
Jiang, et al., "Role of Signal Sequence in Vaccine-Induced Protection against Experimental Coccidioidomycosis", Infection and Immunity, vol. 70, No. 7, pp. 3539-3545, (2002).
Jurcevic, et al., "T cell responses to a mixture of *Mycobacterium tuberculosis* peptides with complementary HLA-DR binding profiles", Clin Exp Immunol, vol. 105, p. 416-421, (1996).
Vordermeier, et al., "The nature of the immunogen determines the specificity of antibodies and T cells to selected peptides of the 38 kDa mycobacterial antigen", International Immunology, vol. 7, No. 4, pp. 559-566, (1995).
International Search Report for corresponding International Application No. PCT/IL2010/000569, mailed May 19, 2011, eight pages.
Kovjazin, et al., "Characterization of Novel Multiantigenic Vaccine Candidates with Pan-HLA Coverage against *Mycobacterium tuberculosis*", Clin. Vaccine Immunol., vol. 20, No. 3, pp. 328-340, (2013).
Rosenberg et al., "Altered CD8+ Responses When Immunizing With Multiepitope Peptide Vaccines", J Immunother., vol. 29, No. 2, pp. 224-231, (2006).
Kovjazin et al., "Autoantibodies against the signal peptide domain of MUC1 in patients with multiple myeloma: Implications for disease diagnosis and prognosis", Experimental and Therapeutic Medicine, vol. 3, pp. 1092-1098, (2012).

(Continued)

*Primary Examiner* — Janet L Andres
*Assistant Examiner* — Barry A Chestnut
(74) *Attorney, Agent, or Firm* — Roberts Mlotkowski Safran Cole & Calderon, P.C.

(57) ABSTRACT

Provided are peptide vaccines including the signal peptide domain of selected target antigens of intracellular pathogens. The peptide vaccines of the invention contain multiple class II and class I-restricted epitopes and are recognized and presented by the majority of the vaccinated human population. Further provided, in particular, are anti tuberculosis vaccines. Also further provided are compositions including the vaccines as well as their use to treat or prevent infection.

12 Claims, 18 Drawing Sheets

(56) References Cited

OTHER PUBLICATIONS

Kovjazin et al., "The use of signal peptide domains as vaccine candidates", Journal: HV; Manuscript #: 2014HV0097R1, 21 pages, (2014).
Database UniProt [Online] Oct. 11, 2004, "RecName: Full-Uncharacterized protein Mb0486; Flags: Precursor", retrieved from EBI accession No. UniProt:P64696 Database accession No. P64696.
Garnier T. et al.: "The Complete Genome Sequence of *Mycobacterium bovis*", Proceedings of the National Academy of Sciences, National Academy of Sciences, US, vol. 100, No. 13, Jun. 24

| SEQ ID | Identity | Target protein | Sequence | Length |
|---|---|---|---|---|
| 1 | VXL-200 | BPBP1 | MKIRLHTLLA VLTAAPLLLA AAGCGS | 26 |
| 2 | VXL-201 | Antigen 85B | MTDVSRKIRA WGRRLMIGTA AAVVLPGLVG LAGGAATAGA | 40 |
| 3 | VXL-203 | Lipoprotein lpqH | MKRGLTVAVA GAAILVAGLS GCSS | 24 |
| 4 | VXL-206 | Hypothetical protein MT0 213 | MKTGTATTRR RLLAVLIALA LPGAAVA | 27 |
| 5 | VXL-207 | Protease | MAAMWRRRPL SSALLSFGLL LGGLPLAAPP LAGA | 34 |
| 6 | VXL-208 | ATP dependet helicase putative | MRFAQPSALS RFSALTRDWF TSTFAAPTAA QA | 32 |
| 7 | VXL-211 | Un char protein Rv0476/MTO4941 prec | MLVLLVAVLV TAVYAFVHA | 19 |
| 8 | VXL-212 | Un char protein Rv1334/MT1376 prec | MLLRKGTVYV LVIRADLVNA MVAHA | 25 |
| 9 | VXL-214 | Putative lipoprotein lpqV prec | MRPSRYAPLL CAMVLALAWL SAVAG | 25 |

| Patient No. | Gender | Ethnic Group | Disease Stage | PPD test | Culture test | MDR resistant |
|---|---|---|---|---|---|---|
| 1 | M | Ethiopian | Latent | 15 mm | Negative | - |
| 2 | M | Ethiopian | Acute | Not done | MTB | N |
| 3 | F | Ethiopian | Acute | Not done | MTB | N |
| 4 | M | Russian | Acute | Not done | MTB | N |
| 5 | M | Ethiopian | Acute | 12 mm | MTB | N |
| 6 | M | Ethiopian | Moderate | Not done | MTB | N |
| 7 | M | Russian | Latent | 20mm | Negative | - |
| 8 | F | Ethiopian | Acute | 22mm | MTB | N |
| 9 | M | Russian | Acute | Not done | MTB | Y |
| 10 | M | Israeli | Acute | Not done | MTB | N |
| 11 | M | Russian | Acute | 15 mm | MTB | Y |
| 12 | M | Israeli | Acute | Not done | MTB | Y |
| 13 | F | Arabic | latent | 20 mm | Negative | - |
| 14 | M | Russian | Acute | Not done | MTB | N |
| 15 | F | Russian | latent | 21 mm | Negative | - |
| 16 | F | Ethiopian | Acute | 18 mm | TBD | N |
| 17 | M | Israeli | Latent | 42 mm | Negative | - |
| 18 | M | Russian | Acute | Not done | MTB | N |
| 19 | M | Russian | Acute | Not done | MTB | N |
| 20 | F | Israeli | Latent | 25 mm | Negative | - |

Fig. 5

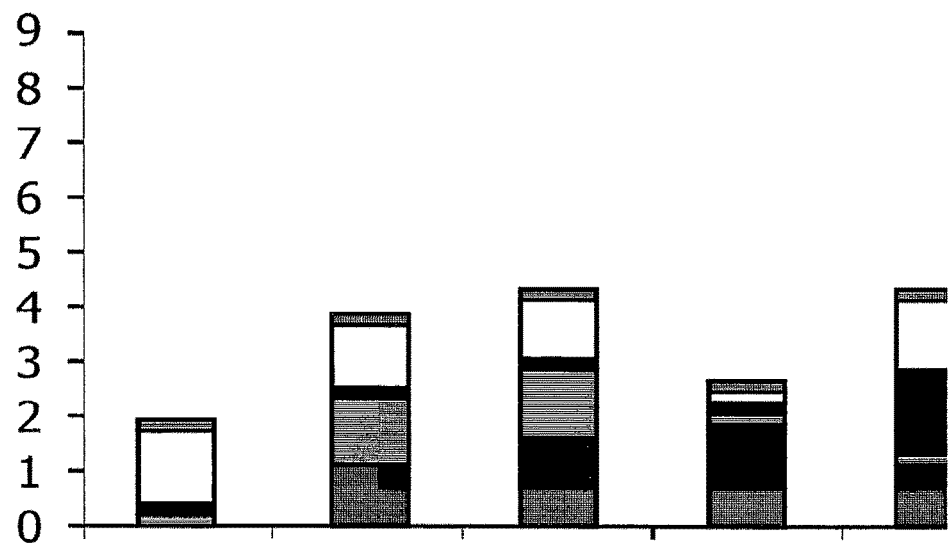
Fig. 7B1
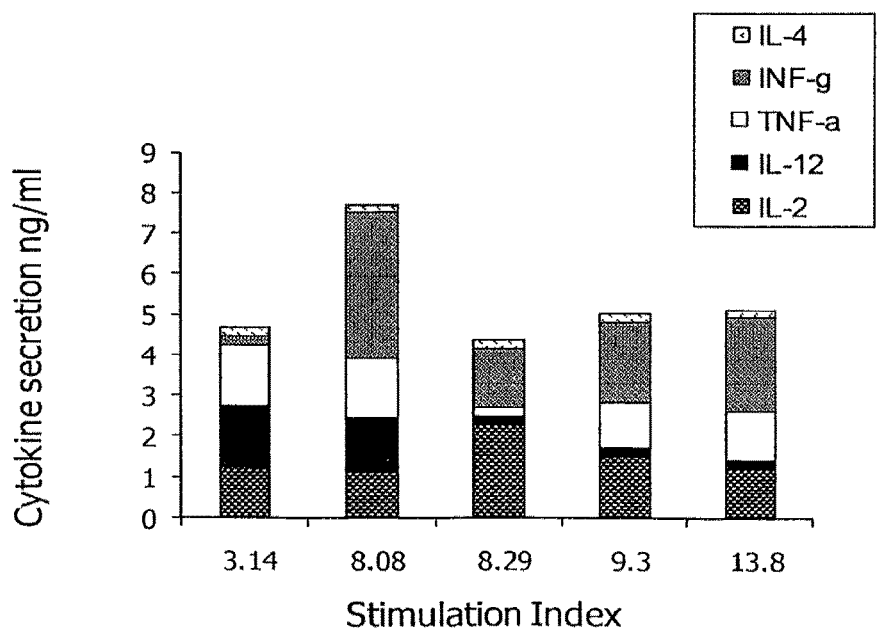
Fig. 7B2

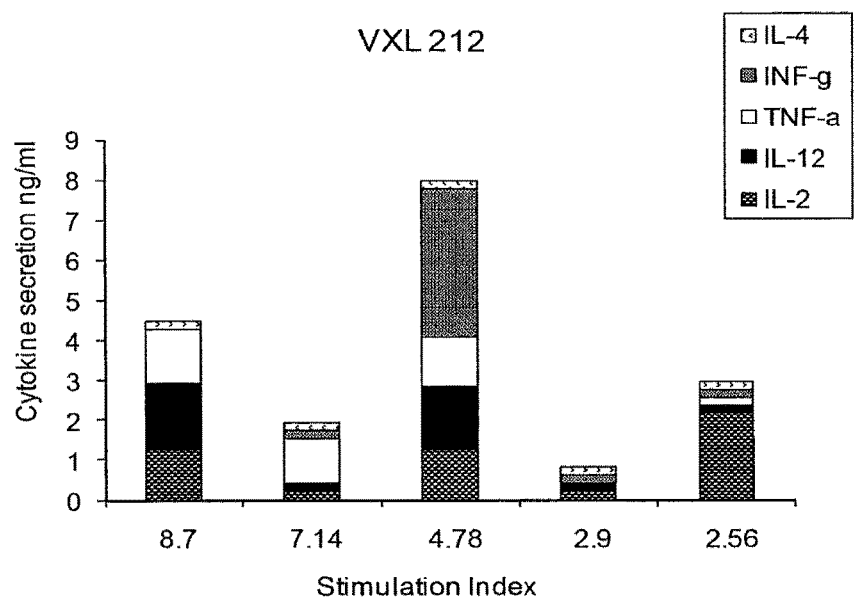
Fig. 7B3
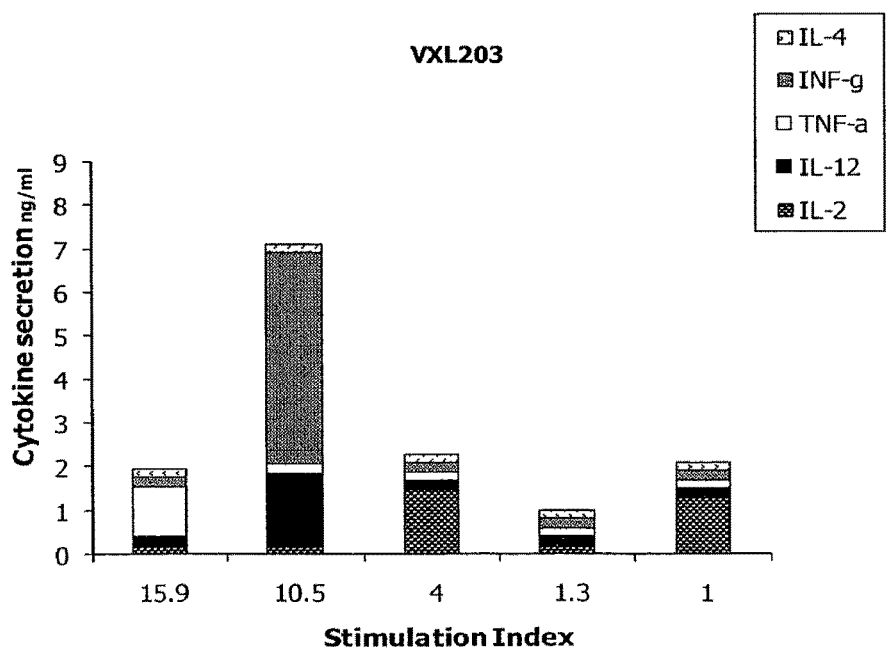
Fig. 7B4

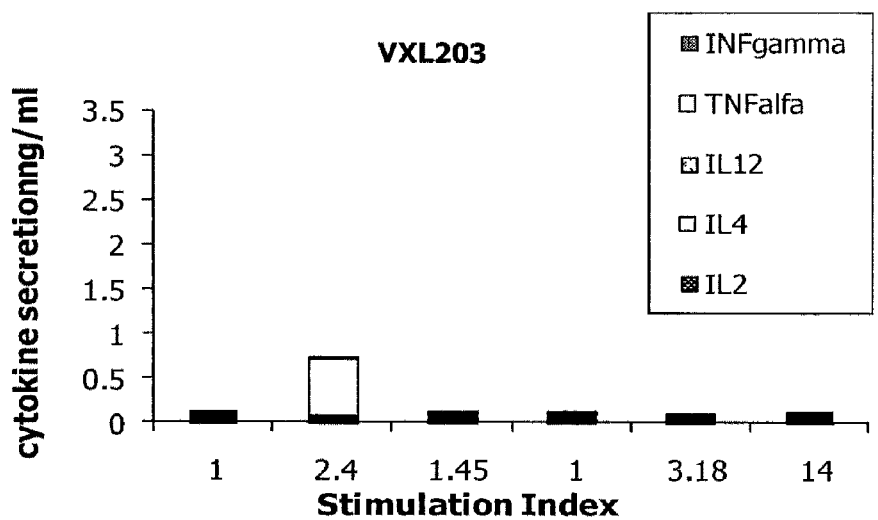
Fig. 8B1
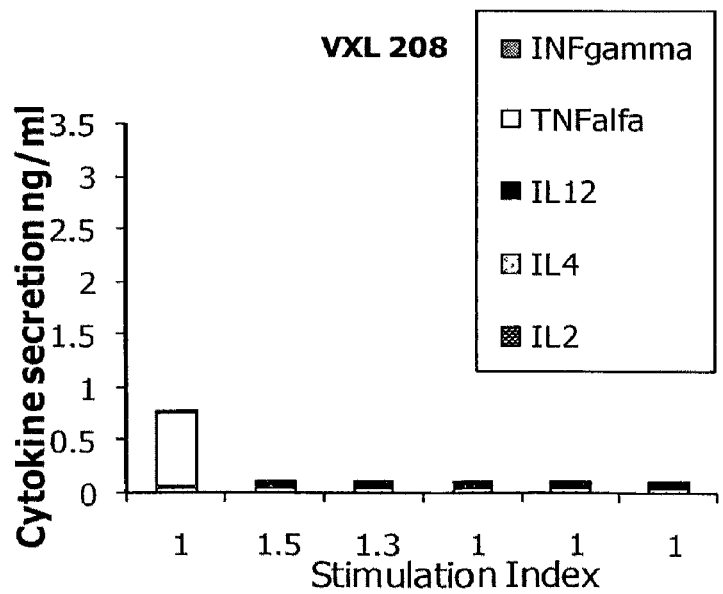
Fig. 8B2

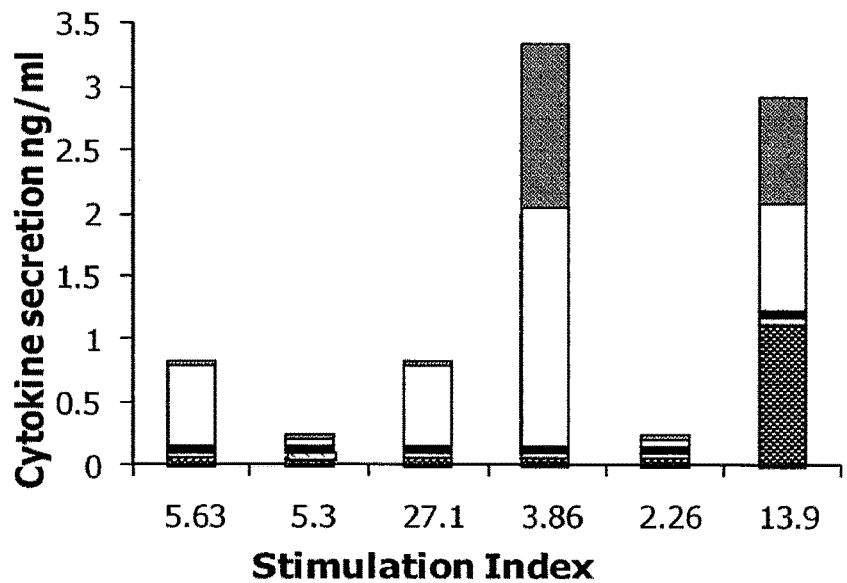
Fig. 8B3
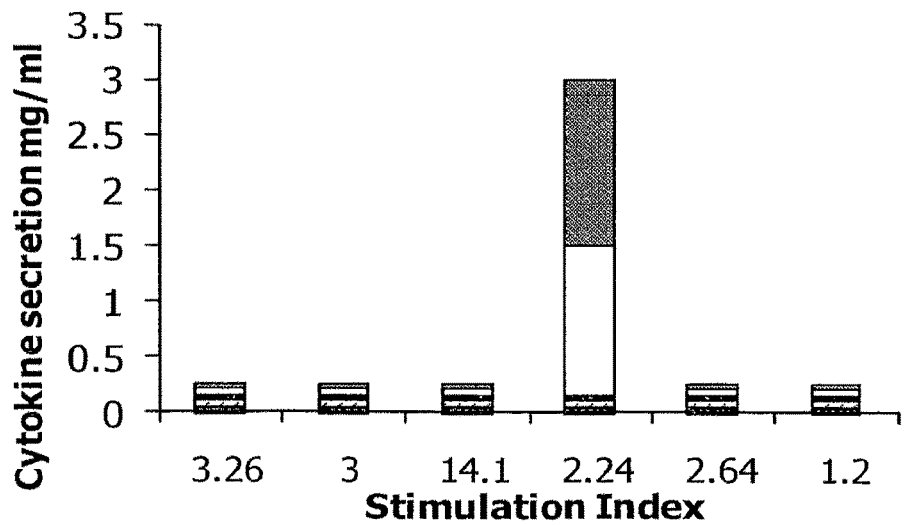
Fig. 8B4

| Donors/patients | Anti–VXL 201 | Anti-VXL 203 | Anti-VXL 208 | Anti-VXL 211 | Anti-VXL 212 |
|---|---|---|---|---|---|
| Donor#12 |  | + |  |  |  |
| Donor#13 |  | + | + | + | + |
| Donor#14 | + | + |  | + |  |
| Donor#15 |  | + | + | + |  |
| Patient#17 | + | + | + | + | + |
| Patient#18 | + | + |  |  | + |
| Patient#19 | + | + |  |  | + |

Fig. 13A

| T-cell lines | Anti-VXL201 | Anti-VXL 203 | Anti-VXL 208 | Anti-VXL 211 | Anti-VXL 212 |
|---|---|---|---|---|---|
| Donors | 85% | 65%-53% | 15% | 60%-38% | 0 |
| Patients | 86%-49% | 94%-73% | 12% | 45% | 16%-4% |

Fig. 13B

| T-cell Line | CD4 T-Cells | | CD8 T-cells | |
|---|---|---|---|---|
|  | $CD44^{high}$ | $CD62L^{high}$ | $CD44^{high}$ | $CD62L^{high}$ |
| Anti-VXL201 | 40.9% | 17 | 79.4 | 11.8 |
| Anti-VXL203 | 40.5-49.2 | 10.5-39.4 | 53-79.7 | 8.2-17.8 |
| Anti-VXL208 | 52.6 | 22 | 50.2 | 32.1 |
| Anti-VXL211 | 38-41 | 6.5-28.7 | 47.6-80 | 4.4-40.9 |
| Naïve PBMC | 0 | 2.1-4 | 1.3-1.5 | 5.9-6 |

Fig. 14

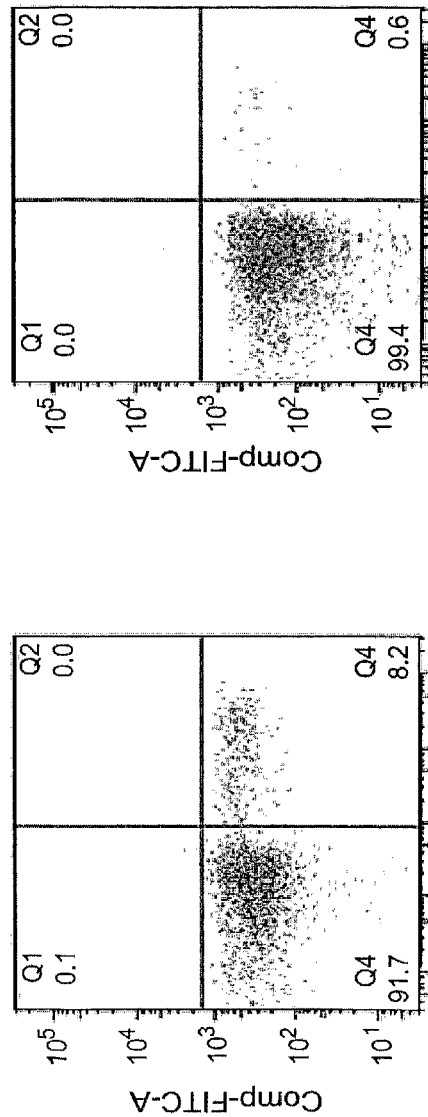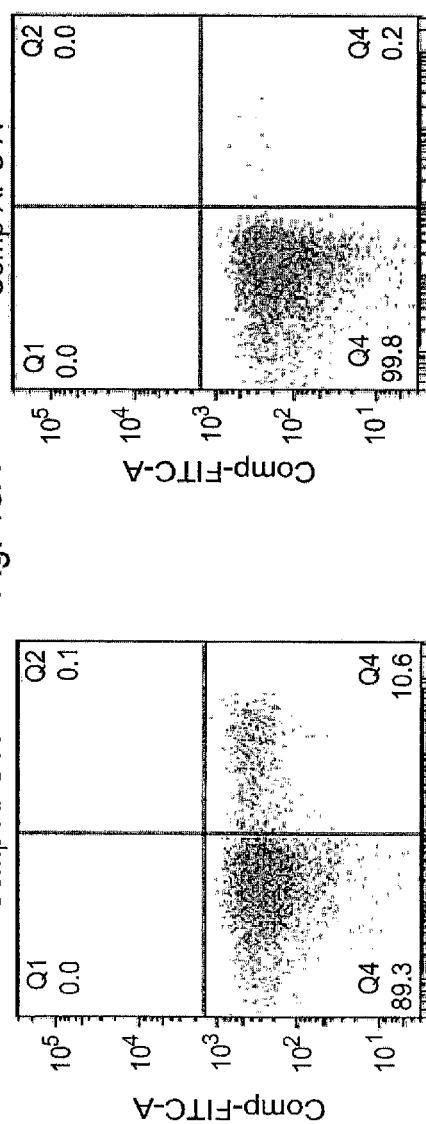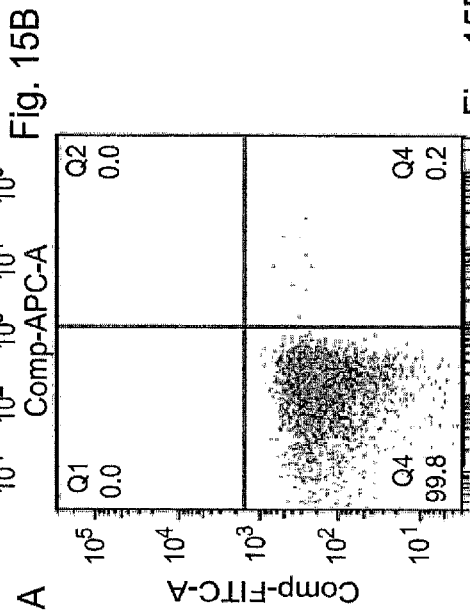

SEQUENCE LISTING

```
<160> NUMBER OF SEQ ID NOS: 56

<210> SEQ ID NO 1
<211> LENGTH: 26
<212> TYPE: PRT
<213> ORGANISM: Mycobacterium tuberculosis

<400> SEQUENCE: 1

Met Lys Ile Arg Leu His Thr Leu Leu Ala Val Leu Thr Ala Ala Pro
1               5                   10                  15

Leu Leu Leu Ala Ala Ala Gly Cys Gly Ser
            20                  25

<210> SEQ ID NO 2
<211> LENGTH: 40
<212> TYPE: PRT
<213> ORGANISM: Mycobacterium tuberculosis

<400> SEQUENCE: 2

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala
        35                  40

<210> SEQ ID NO 3
<211> LENGTH: 38
<212> TYPE: PRT
<213> ORGANISM: Mycobacterium leprae

<400> SEQUENCE: 3

Met Ile Asp Val Ser Gly Lys Ile Arg Ala Trp Gly Arg Trp Leu Leu
1               5                   10                  15

Val Gly Ala Ala Ala Thr Leu Pro Ser Leu Ile Ser Leu Ala Gly Gly
            20                  25                  30

Ala Ala Thr Ala Ser Ala
        35
```

<210> SEQ ID NO 4
<211> LENGTH: 24
<212> TYPE: PRT
<213> ORGANISM: Mycobacterium tuberculosis

<400> SEQUENCE: 4

Met Lys Arg Gly Leu Thr Val Ala Val Ala Gly Ala Ala Ile Leu Val
1               5                   10                  15
Ala Gly Leu Ser Gly Cys Ser Ser
            20

<210> SEQ ID NO 5
<211> LENGTH: 27
<212> TYPE: PRT
<213> ORGANISM: Mycobacterium leprae

<400> SEQUENCE: 5

Met Arg His Lys Leu Leu Ala Ala Ile Tyr Ala Val Thr Ile Met Ala
1               5                   10                  15
Gly Ala Ala Gly Cys Ser Gly Gly Thr Gln Ala
            20                  25

<210> SEQ ID NO 6
<211> LENGTH: 31
<212> TYPE: PRT
<213> ORGANISM: Mycobacterium tuberculosis

<400> SEQUENCE: 6

Met Leu Met Pro Glu Met Asp Arg Arg Arg Met Met Met Ala Gly
1               5                   10                  15
Phe Gly Ala Leu Ala Ala Ala Leu Pro Ala Pro Thr Ala Trp Ala
            20                  25                  30

<210> SEQ ID NO 7
<211> LENGTH: 27
<212> TYPE: PRT
<213> ORGANISM: Mycobacterium tuberculosis

<400> SEQUENCE: 7

Met Lys Thr Gly Thr Ala Thr Thr Arg Arg Arg Leu Leu Ala Val Leu
1               5                   10                  15
Ile Ala Leu Ala Leu Pro Gly Ala Ala Val Ala
            20                  25

<210> SEQ ID NO 8
<211> LENGTH: 34
<212> TYPE: PRT
<213> ORGANISM: Mycobacterium tuberculosis

<400> SEQUENCE: 8

Met Ala Ala Met Trp Arg Arg Arg Pro Leu Ser Ser Ala Leu Leu Ser
1               5                   10                  15
Phe Gly Leu Leu Leu Gly Gly Leu Pro Leu Ala Ala Pro Pro Leu Ala
            20                  25                  30
Gly Ala

<210> SEQ ID NO 9
<211> LENGTH: 32
<212> TYPE: PRT
<213> ORGANISM: Mycobacterium tuberculosis

<400> SEQUENCE: 9

```
Met Arg Phe Ala Gln Pro Ser Ala Leu Ser Arg Phe Ser Ala Leu Thr
1               5                   10                  15

Arg Asp Trp Phe Thr Ser Thr Phe Ala Ala Pro Thr Ala Ala Gln Ala
                20                  25                  30

<210> SEQ ID NO 10
<211> LENGTH: 37
<212> TYPE: PRT
<213> ORGANISM: Mycobacterium tuberculosis

<400> SEQUENCE: 10

Met Leu Ser Arg Thr Arg Phe Ser Met Gln Arg Gln Met Lys Arg Val
1               5                   10                  15

Ile Ala Gly Ala Phe Ala Val Trp Leu Val Gly Trp Ala Gly Gly Phe
                20                  25                  30

Gly Thr Ala Ile Ala
            35

<210> SEQ ID NO 11
<211> LENGTH: 23
<212> TYPE: PRT
<213> ORGANISM: Mycobacterium tuberculosis

<400> SEQUENCE: 11

Met Arg Ile Lys Ile Phe Met Leu Val Thr Ala Val Val Leu Leu Cys
1               5                   10                  15

Cys Ser Gly Val Ala Thr Ala
                20

<210> SEQ ID NO 12
<211> LENGTH: 19
<212> TYPE: PRT
<213> ORGANISM: Mycobacterium tuberculosis

<400> SEQUENCE: 12

Met Leu Val Leu Leu Val Ala Val Leu Val Thr Ala Val Tyr Ala Phe
1               5                   10                  15

Val His Ala

<210> SEQ ID NO 13
<211> LENGTH: 25
<212> TYPE: PRT
<213> ORGANISM: Mycobacterium tuberculosis

<400> SEQUENCE: 13

Met Leu Leu Arg Lys Gly Thr Val Tyr Val Leu Val Ile Arg Ala Asp
1               5                   10                  15

Leu Val Asn Ala Met Val Ala His Ala
                20                  25

<210> SEQ ID NO 14
<211> LENGTH: 24
<212> TYPE: PRT
<213> ORGANISM: Mycobacterium tuberculosis

<400> SEQUENCE: 14

Met Arg Arg Lys Val Arg Arg Leu Thr Leu Ala Val Ser Ala Leu Val
1               5                   10                  15

Ala Leu Phe Pro Ala Val Ala Gly
                20
```

```
<210> SEQ ID NO 15
<211> LENGTH: 25
<212> TYPE: PRT
<213> ORGANISM: Mycobacterium tuberculosis

<400> SEQUENCE: 15

Met Arg Pro Ser Arg Tyr Ala Pro Leu Leu Cys Ala Met Val Leu Ala
1               5                   10                  15

Leu Ala Trp Leu Ser Ala Val Ala Gly
            20                  25

<210> SEQ ID NO 16
<211> LENGTH: 30
<212> TYPE: PRT
<213> ORGANISM: Mycobacterium tuberculosis

<400> SEQUENCE: 16

Met Arg Asn Arg Gly Phe Gly Arg Arg Glu Leu Leu Val Ala Met Ala
1               5                   10                  15

Met Leu Val Ser Val Thr Gly Cys Ala Arg His Ala Ser Gly
            20                  25                  30

<210> SEQ ID NO 17
<211> LENGTH: 18
<212> TYPE: PRT
<213> ORGANISM: Plasmodium falciparum

<400> SEQUENCE: 17

Met Met Arg Lys Leu Ala Ile Leu Ser Val Ser Ser Phe Leu Phe Val
1               5                   10                  15

Glu Ala

<210> SEQ ID NO 18
<211> LENGTH: 22
<212> TYPE: PRT
<213> ORGANISM: Plasmodium falciparum

<400> SEQUENCE: 18

Met Lys Ile Leu Ser Val Phe Phe Leu Val Leu Phe Phe Ile Ile Phe
1               5                   10                  15

Asn Lys Glu Ser Leu Ala
            20

<210> SEQ ID NO 19
<211> LENGTH: 23
<212> TYPE: PRT
<213> ORGANISM: Plasmodium falciparum

<400> SEQUENCE: 19

Met Lys His Ile Leu Tyr Ile Ser Phe Tyr Phe Ile Leu Val Asn Leu
1               5                   10                  15

Leu Ile Phe His Ile Asn Gly
            20

<210> SEQ ID NO 20
<211> LENGTH: 25
<212> TYPE: PRT
<213> ORGANISM: Plasmodium falciparum

<400> SEQUENCE: 20

Met Asn His Leu Gly Asn Val Lys Tyr Leu Val Ile Val Phe Leu Ile
1               5                   10                  15
```

```
Phe Phe Asp Leu Phe Leu Val Asn Gly
        20                  25

<210> SEQ ID NO 21
<211> LENGTH: 20
<212> TYPE: PRT
<213> ORGANISM: Plasmodium falciparum

<400> SEQUENCE: 21

Met Lys Ile Ile Phe Phe Leu Cys Ser Phe Leu Phe Phe Ile Ile Asn
1               5                   10                  15

Thr Gln Cys Val
        20

<210> SEQ ID NO 22
<211> LENGTH: 25
<212> TYPE: PRT
<213> ORGANISM: Plasmodium falciparum

<400> SEQUENCE: 22

Met Asn Ile Arg Lys Phe Ile Pro Ser Leu Ala Leu Met Leu Ile Phe
1               5                   10                  15

Phe Ala Phe Ala Asn Leu Val Leu Ser
        20                  25

<210> SEQ ID NO 23
<211> LENGTH: 24
<212> TYPE: PRT
<213> ORGANISM: Plasmodium vivax

<400> SEQUENCE: 23

Met Thr Ser Leu Arg Asn Met Arg Val Phe Phe Leu Phe Val Leu Leu
1               5                   10                  15

Phe Ile Ser Lys Asn Val Ile Gly
        20

<210> SEQ ID NO 24
<211> LENGTH: 23
<212> TYPE: PRT
<213> ORGANISM: Plasmodium vivax

<400> SEQUENCE: 24

Met Arg Ile Ala Lys Ala Ala Leu Cys Gly Gln Leu Leu Ile Trp Trp
1               5                   10                  15

Leu Ser Ala Pro Ala Glu Gly
        20

<210> SEQ ID NO 25
<211> LENGTH: 21
<212> TYPE: PRT
<213> ORGANISM: Plasmodium vivax

<400> SEQUENCE: 25

Met Lys Val Ser Tyr Ile Leu Ser Leu Phe Phe Phe Leu Ile Ile Tyr
1               5                   10                  15

Lys Asn Thr Thr Thr
        20

<210> SEQ ID NO 26
<211> LENGTH: 21
<212> TYPE: PRT
<213> ORGANISM: Plasmodium vivax
```

<400> SEQUENCE: 26

Met Lys Leu Leu Ala Ala Val Phe Leu Leu Phe Cys Ala Ile Leu Cys
1               5                   10                  15

Asn His Ala Leu Gly
            20

<210> SEQ ID NO 27
<211> LENGTH: 22
<212> TYPE: PRT
<213> ORGANISM: Plasmodium vivax

<400> SEQUENCE: 27

Met Lys Asn Phe Ile Leu Leu Ala Val Ser Ser Ile Leu Leu Val Asp
1               5                   10                  15

Leu Phe Pro Thr His Cys
            20

<210> SEQ ID NO 28
<211> LENGTH: 23
<212> TYPE: PRT
<213> ORGANISM: Plasmodium vivax

<400> SEQUENCE: 28

Met Lys His Thr Arg Ser Val Thr Leu Tyr Leu Phe Leu Leu Thr Leu
1               5                   10                  15

Cys Ala Tyr Leu Thr Gly Ala
            20

<210> SEQ ID NO 29
<211> LENGTH: 23
<212> TYPE: PRT
<213> ORGANISM: Plasmodium vivax

<400> SEQUENCE: 29

Met Asn Lys Ser Phe Leu Leu Ile Ala Ser Tyr Phe Cys Leu Val Val
1               5                   10                  15

His Leu Gly Thr Val Ile Ala
            20

<210> SEQ ID NO 30
<211> LENGTH: 24
<212> TYPE: PRT
<213> ORGANISM: Toxoplasma gondii

<400> SEQUENCE: 30

Met Val Arg Val Ser Ala Ile Val Gly Ala Ala Ala Ser Val Phe Val
1               5                   10                  15

Cys Leu Ser Ala Gly Ala Tyr Ala
            20

<210> SEQ ID NO 31
<211> LENGTH: 39
<212> TYPE: PRT
<213> ORGANISM: Toxoplasma gondii

<400> SEQUENCE: 31

Met Ser Val Ser Leu His His Phe Ile Ile Ser Ser Gly Phe Leu Thr
1               5                   10                  15

Ser Met Phe Pro Lys Ala Val Arg Arg Ala Val Thr Ala Gly Val Phe
            20                  25                  30

```
Ala Ala Pro Thr Leu Met Ser
         35

<210> SEQ ID NO 32
<211> LENGTH: 30
<212> TYPE: PRT
<213> ORGANISM: Toxoplasma gondii

<400> SEQUENCE: 32

Met Phe Pro Lys Ala Val Arg Arg Ala Val Thr Ala Gly Val Phe Ala
1               5                   10                  15

Ala Pro Thr Leu Met Ser Phe Leu Leu Cys Gly Val Met Ala
            20                  25                  30

<210> SEQ ID NO 33
<211> LENGTH: 26
<212> TYPE: PRT
<213> ORGANISM: Toxoplasma gondii

<400> SEQUENCE: 33

Met Ser Phe Ser Lys Thr Thr Ser Leu Ala Ser Leu Ala Leu Thr Gly
1               5                   10                  15

Leu Phe Val Val Phe Gln Phe Ala Leu Ala
            20                  25

<210> SEQ ID NO 34
<211> LENGTH: 28
<212> TYPE: PRT
<213> ORGANISM: Toxoplasma gondii

<400> SEQUENCE: 34

Met Gly Arg Pro Arg Trp Pro Leu Pro Ser Met Phe Phe Leu Ser Leu
1               5                   10                  15

Leu Cys Val Ser Glu Lys Arg Phe Ser Val Ser Gly
            20                  25

<210> SEQ ID NO 35
<211> LENGTH: 17
<212> TYPE: PRT
<213> ORGANISM: Human herpesvirus 4

<400> SEQUENCE: 35

Met Gln Leu Leu Cys Val Phe Cys Leu Val Leu Leu Trp Glu Val Gly
1               5                   10                  15

Ala

<210> SEQ ID NO 36
<211> LENGTH: 23
<212> TYPE: PRT
<213> ORGANISM: Human herpesvirus 4

<400> SEQUENCE: 36

Met Glu Arg Arg Leu Val Val Thr Leu Gln Cys Leu Val Leu Leu Tyr
1               5                   10                  15

Leu Ala Pro Glu Cys Gly Gly
            20

<210> SEQ ID NO 37
<211> LENGTH: 25
<212> TYPE: PRT
<213> ORGANISM: Human cytomegalovirus

<400> SEQUENCE: 37
```

```
Met Glu Ser Arg Ile Trp Cys Leu Val Val Cys Val Asn Leu Cys Ile
1               5                   10                  15

Val Cys Leu Gly Ala Ala Val Ser Ser
            20                  25
```

<210> SEQ ID NO 38
<211> LENGTH: 30
<212> TYPE: PRT
<213> ORGANISM: Human cytomegalovirus

<400> SEQUENCE: 38

```
Met Arg Arg Ile Ser Leu Thr Ser Ser Pro Val Arg Leu Leu Leu Phe
1               5                   10                  15

Leu Leu Leu Leu Leu Ile Ala Leu Glu Ile Met Tyr Asn Ser
            20                  25                  30
```

<210> SEQ ID NO 39
<211> LENGTH: 21
<212> TYPE: PRT
<213> ORGANISM: Human cytomegalovirus

<400> SEQUENCE: 39

```
Met Arg Arg Trp Leu Arg Leu Leu Val Gly Leu Gly Cys Cys Trp Val
1               5                   10                  15

Thr Leu Ala His Ala
            20
```

<210> SEQ ID NO 40
<211> LENGTH: 27
<212> TYPE: PRT
<213> ORGANISM: Human cytomegalovirus

<400> SEQUENCE: 40

```
Met Ile Leu Trp Ser Pro Ser Thr Cys Ser Phe Phe Trp His Trp Cys
1               5                   10                  15

Leu Ile Ala Val Ser Val Leu Ser Ser Arg Ser
            20                  25
```

<210> SEQ ID NO 41
<211> LENGTH: 27
<212> TYPE: PRT
<213> ORGANISM: Human cytomegalovirus

<400> SEQUENCE: 41

```
Met Arg Ile Gln Leu Leu Leu Val Ala Thr Leu Val Ala Ser Ile Val
1               5                   10                  15

Ala Thr Arg Val Glu Asp Met Ala Thr Phe Arg
            20                  25
```

<210> SEQ ID NO 42
<211> LENGTH: 22
<212> TYPE: PRT
<213> ORGANISM: Homo sapiens

<400> SEQUENCE: 42

```
Met Ala Asn Leu Gly Cys Trp Met Leu Val Leu Phe Val Ala Thr Trp
1               5                   10                  15

Ser Asp Leu Gly Leu Cys
            20
```

<210> SEQ ID NO 43

```
<211> LENGTH: 30
<212> TYPE: PRT
<213> ORGANISM: Human immunodeficiency virus

<400> SEQUENCE: 43

Met Arg Val Lys Glu Lys Tyr Gln His Leu Trp Arg Trp Gly Trp Lys
1               5                   10                  15

Trp Gly Thr Met Leu Leu Gly Ile Leu Met Ile Cys Ser Ala
            20                  25                  30

<210> SEQ ID NO 44
<211> LENGTH: 25
<212> TYPE: PRT
<213> ORGANISM: Human immunodeficiency virus

<400> SEQUENCE: 44

Met Arg Leu Gly Pro Arg Thr Ala Ala Leu Gly Leu Leu Leu Leu Cys
1               5                   10                  15

Ala Ala Ala Ala Gly Ala Gly Lys Ala
            20                  25

<210> SEQ ID NO 45
<211> LENGTH: 29
<212> TYPE: PRT
<213> ORGANISM: Human immunodeficiency virus

<400> SEQUENCE: 45

Met Ala Leu Ala Val Ser Leu Pro Leu Ala Leu Ser Pro Pro Arg Leu
1               5                   10                  15

Leu Leu Leu Leu Leu Ser Leu Leu Pro Val Ala Arg Ala
            20                  25

<210> SEQ ID NO 46
<211> LENGTH: 29
<212> TYPE: PRT
<213> ORGANISM: Human immunodeficiency virus

<400> SEQUENCE: 46

Met Arg Ala Thr Glu Ile Arg Lys Asn Tyr Gln His Leu Trp Lys Gly
1               5                   10                  15

Gly Thr Leu Leu Leu Gly Met Leu Met Ile Cys Ser Ala
            20                  25

<210> SEQ ID NO 47
<211> LENGTH: 29
<212> TYPE: PRT
<213> ORGANISM: Human immunodeficiency virus

<400> SEQUENCE: 47

Met Arg Val Lys Gly Ile Arg Arg Asn Tyr Gln His Trp Trp Gly Trp
1               5                   10                  15

Gly Thr Met Leu Leu Gly Leu Leu Met Ile Cys Ser Ala
            20                  25

<210> SEQ ID NO 48
<211> LENGTH: 18
<212> TYPE: PRT
<213> ORGANISM: Human immunodeficiency virus

<400> SEQUENCE: 48

Met Leu Leu Cys Ile Val Cys Ser Leu Leu Val Cys Phe Pro Lys Leu
1               5                   10                  15
```

-continued

Leu Ser

<210> SEQ ID NO 49
<211> LENGTH: 26
<212> TYPE: PRT
<213> ORGANISM: human herpesvirus 1

<400> SEQUENCE: 49

Met Ser Ser Thr Gln Ile Arg Thr Glu Ile Pro Val Ala Leu Leu Ile
1               5                   10                  15

Leu Cys Leu Cys Leu Val Ala Cys His Ala
            20                  25

<210> SEQ ID NO 50
<211> LENGTH: 22
<212> TYPE: PRT
<213> ORGANISM: Hepatitis C virus

<400> SEQUENCE: 50

Met Asp Ser Leu Ala Ser Leu Val Leu Cys Gly Val Ser Leu Leu Leu
1               5                   10                  15

Ser Gly Thr Val Glu Gly
            20

<210> SEQ ID NO 51
<211> LENGTH: 18
<212> TYPE: PRT
<213> ORGANISM: Hepatitis C virus

<400> SEQUENCE: 51

Met Glu Lys Leu Leu Cys Phe Leu Val Leu Thr Ser Leu Ser His Ala
1               5                   10                  15

Phe Gly

<210> SEQ ID NO 52
<211> LENGTH: 17
<212> TYPE: PRT
<213> ORGANISM: Influenza virus

<400> SEQUENCE: 52

Met Lys Ala Asn Leu Leu Val Leu Leu Cys Ala Leu Ala Ala Ala Asp
1               5                   10                  15

Ala

<210> SEQ ID NO 53
<211> LENGTH: 16
<212> TYPE: PRT
<213> ORGANISM: Influenza virus

<400> SEQUENCE: 53

Met Lys Thr Thr Ile Ile Leu Ile Leu Leu Thr His Trp Val Tyr Ser
1               5                   10                  15

<210> SEQ ID NO 54
<211> LENGTH: 26
<212> TYPE: PRT
<213> ORGANISM: Influenza virus

<400> SEQUENCE: 54

Met Leu Pro Ser Thr Val Gln Thr Leu Thr Leu Leu Leu Thr Ser Gly
1               5                   10                  15

Gly Val Leu Leu Ser Leu Tyr Val Ser Ala

<210> SEQ ID NO 55
<211> LENGTH: 330
<212> TYPE: PRT
<213> ORGANISM: Artificial Sequence
<220> FEATURE:
<223> OTHER INFORMATION: bacterial sequences plus additional amino acids

<400> SEQUENCE: 55

```
Thr Met Gly Ser Gly Gly Ser Gly Ala Ser Gly Gly Ser Gly Lys Lys
1               5                   10                  15

Lys Lys Lys Lys Lys Lys Met Leu Leu Arg Lys Gly Thr Val Tyr Val
            20                  25                  30

Leu Val Ile Arg Ala Asp Leu Val Asn Ala Met Val Ala His Ala Lys
        35                  40                  45

Lys Lys Gly Gly Ser Gly Ala Ser Gly Gly Ser Gly Gly Ala Ser Gly
    50                  55                  60

Ala Ser Gly Gly Ser Gly Lys Lys Lys Lys Lys Lys Lys Lys Lys Met
65                  70                  75                  80

Leu Val Leu Leu Val Ala Val Leu Val Thr Ala Val Tyr Ala Phe Val
                85                  90                  95

His Ala Lys Lys Lys Gly Gly Ser Gly Ala Ser Gly Gly Ser Gly Gly
            100                 105                 110

Gly Ser Gly Ala Ser Gly Gly Ser Gly Gly Ser Gly Gly Ser Gly Gly
            115                 120                 125

Gly Lys Lys Lys Lys Lys Lys Lys Lys Met Arg Phe Ala Gln Pro
130                 135                 140

Ser Ala Leu Ser Arg Phe Ser Ala Leu Thr Arg Asp Trp Phe Thr Ser
145                 150                 155                 160

Thr Phe Ala Ala Pro Thr Ala Ala Gln Ala Lys Lys Gly Gly Ser
                165                 170                 175

Gly Ala Ser Gly Gly Ser Gly Gly Gly Ser Gly Ala Ser Gly Val Asp
            180                 185                 190

Thr Ser Gly Ser Gly Gly Ser Gly Gly Gly Ser Gly Gly Lys Lys Lys
        195                 200                 205

Lys Lys Lys Lys Lys Met Lys Arg Gly Leu Thr Val Ala Val Ala
    210                 215                 220

Gly Ala Ala Ile Leu Val Ala Gly Leu Ser Gly Cys Ser Ser Lys Lys
225                 230                 235                 240

Lys Gly Gly Ser Gly Gly Ser Gly Gly Gly Ser Gly Ala Ser Gly
            245                 250                 255

Gly Ser Gly Gly Gly Ser Gly Ala Ser Gly Gly Ser Gly Gly Gly Ser
        260                 265                 270

Gly Ala Ser Gly Gly Ser Gly Lys Lys Lys Lys Lys Lys Lys Lys
    275                 280                 285

Met Thr Asp Val Ser Arg Lys Ile Arg Ala Trp Gly Arg Arg Leu Met
    290                 295                 300

Ile Gly Thr Ala Ala Ala Val Val Leu Pro Gly Leu Val Gly Leu Ala
305                 310                 315                 320

Gly Gly Ala Ala Thr Ala Gly Ala Leu Glu
                325                 330
```

<210> SEQ ID NO 56
<211> LENGTH: 989
<212> TYPE: DNA

```
<213> ORGANISM: Artificial Sequence
<220> FEATURE:
<223> OTHER INFORMATION: bacterial sequences

<400> SEQUENCE: 56
ccatgggtag tggcggatct ggcgcgagtg gcgggagtgg gaaaaagaaa aaaaagaaaa      60
agaaaatgct gttacgtaaa ggcaccgttt atgtgctggt cattcgcgcc gatcttgtga     120
atgcgatggt tgcacatgcg aaaaagaaag gtggcagtgg tgcctctgga ggttctgggg     180
gtgctagcgg cgcgagtggt gggagcggga agaaaaaaaa gaaaaagaaa aagaaaatgc     240
ttgtgctgct cgttgcggtt ctggtgaccg ccgtctacgc atttgtccat gcgaaaaaga     300
aaggtggctc aggagccagt ggtggaagcg ggggtggctc cggggcgagc ggtggatctg     360
gcggagggtc tggcagcggc ggtgggaaaa agaagaaaaa aaagaaaaag aaaatgcgtt     420
tcgcacagcc gagcgcgctg tctcgcttta gtgcactgac ccgtgattgg tttacgagca     480
ccttcgccgc gccgactgcg gcacaggcta agaaaaaagg cggttctggg gcgtcaggcg     540
ggagcggcgg aggatcaggt gcctctggtg tcgacactag tggcagtgga gggtctggtg     600
gaggctctgg tggcaaaaaa aagaaaaaga aaaagaaaaa gatgaaacgt ggcctgaccg     660
ttgcggtggc aggtgcggcc attctggtgg caggtctgag cggctgctct agtaagaaaa     720
aaggagggag cggcggttcg ggcggtggag ggagcggtgc ctctggcggt tcaggtggcg     780
gaagtggggc atccggcggt tccggcggtg gaagcggtgc ctctggaggc agtggtaaga     840
aaaagaaaaa gaaaaaaaag aaaatgaccg atgttagccg caaatccgt gcctggggcc      900
gtcgcctgat gatcggcacc gcagctgcgg ttgtgctgcc gggtctggtt ggccttgcag     960
gtggcgccgc gaccgcaggc gcgctcgag                                       989
```

ANTIGEN SPECIFIC MULTI EPITOPE-BASED ANTI-INFECTIVE VACCINES

This is a National Phase Application filed under 35 U.S.C. §371 as a national stage of PCT/IL2010/000569, filed on Jul. 15, 2010, an application claiming the benefit under 35 U.S.C. §119(e) of U.S. Provisional Application No. 61/225,957, filed on Jul. 16, 2009, the content of each of which is hereby incorporated by reference in their entirety.

FIELD OF THE INVENTION

The present invention relates to peptide vaccines directed against intracellular pathogens with pan HLA class I and class II binding properties, as well as to pharmaceutical compositions containing the peptide vaccines and methods for treating or preventing infections caused by intracellular pathogens.

"The Sequence Listing submitted in text format (.txt) on Mar. 27, 2012, named "2137157_ST25.txt", (created on Monday, Mar. 12, 2012, 20.3 KB), is incorporated herein by reference."

BACKGROUND

Intracellular pathogens are the main cause for increased morbidity and mortality worldwide. The list of intracellular infectious agents that have had a significant impact on global health and economy includes viral pathogens such as human immunodeficiency virus (HIV), hepatitis B and C virus (HBV and HCV), Influenza, Epstein Barr virus (EBV), protozoan parasites which are the causative agents of Chagas disease, Malaria, *Toxoplasma* and Leishmaniasis and bacterial pathogens including agents responsible for Tuberculosis (TB), Chlamydia and Leprosy. In spite of decades of research, there is very little progress in the development of effective vaccines against these pathogens, most of the vaccines being the live attenuated pathogens.

*Mycobacterium tuberculosis* (Mtb) is one of the most ubiquitous pathogens in the world. It is estimated that roughly one third of the world's population is infected, resulting in 3 million deaths per year. Tuberculosis continues to be a major public health issue in many parts of the world due to a) the relatively long period of treatment required to cure it, b) the emergence of drug-resistant strains and c) the rise in HIV infection as a cofactor that facilitates the transmission and progression of the disease.

Currently, a live attenuated strain of *Mycobacterium bovis* (BCG) is used as a vaccine for children. However, this is not sufficiently effective as it has variable efficiency (0-80%), immunity tends to wane after 10-15 years and it fails to control dormant or new infection.

Despite this, BCG still has value for example in its efficacy against meningeal TB and leprosy. Nevertheless, a more effective vaccine is essential in order to control the spread of TB more effectively. In particular, there is a demand for more effective preventive "pre infection" vaccines as well as "post infection" vaccines that could be administered against a background of BCG immunization and/or pre-existing Mtb infection.

WO 2008/035350 discloses signal peptide based therapeutic vaccine compositions targeted against various tumor associated antigens.

SUMMARY OF THE INVENTION

The present invention provides an antigen specific peptide vaccine which is able to induce strong, comprehensive response in the majority of the population against a target pathogen. More specifically, but without wishing to be limited to a single hypothesis, such a vaccine preferably combines activation of both $CD4^+$ and $CD8^+$ T cells via multiple class II and class I-restricted epitopes which are present within the internal sequences of the vaccine and are derived from the same antigen, and will lead to inhibition of intracellular development of the pathogen thereby preventing infection.

The present invention thus provides a peptide vaccine comprising at least one signal peptide domain of at least one target protein of an intracellular pathogen or a pathogen-induced host protein wherein said signal peptide domain is recognized and presented by more than 50% of the MHC (major histocompatibility complex) class I and MHC Class II alleles in the vaccinated human population.

In one aspect, the present invention relates to peptide vaccines comprising at least one signal peptide domain of at least one target antigen of an intracellular pathogen.

In one embodiment, the present invention relates to peptide vaccines consisting of at least one signal peptide domain of at least one target antigen of an intracellular pathogen.

In one embodiment the peptide vaccines of the invention comprise at least one signal peptide of proteins selected from the group consisting of the Tuberculosis antigens—BPBP1, Antigen 85B, Antigen 85B—Precursor, Lipoprotein lpqH, Putative lipoprotein IprB precursor, Putative lipoprotein IpqV precursor, Beta gluconase putative, Hypothetical protein MTO 213, Protease, ATP dependent helicase putative, Hypothetical protein MT1221, BCG, Hypothetical protein Rv0476/MT04941 precursor, Hypothetical protein Rv1334/MT1376 precursor, beta-Lactomase precursor; the Malaria *P. Falciparum* antigens—Circumsporozoit protein precursor, Malaria exported protein-1, Liver stage antigen (LSA-1), Sporozoit surface antigen 2, MSP1, Protein Antigen; the Malaria *P. Vivax* antigens—Cytoadherence linked asexual protein, Membrane protein PF12, Exported protein 2, Circumsporozoite-protein related antigen, Circumsporozoite protein precursor, Merozoite surface protein 3 alfa, CTRP adhesive protein invasive stage; The *Toxoplasma gondii* antigens—GRA-1, SAG1, Surface antigen SAG1, Surface Antigen P22, Rhoptry protein 10; The EBV antigens—Glycoprotein GP85 and BCRF-1, the CMV antigens, Glycoprotein B, RAE-1 (human), Unique short US8 glycoprotein precursor, US9 Protein, US7; the human Prion protein; the HIV antigens—Envelope Glycoprotein, reticulocalbin-2 precursor (human), neuronalacetycholine reccep. alfa 3 (human), Envelope polyprotein GP'160 precursor and Transforming membrane receptor-like protein; the Herpes virus 8 antigen—HHV-8 glycoprotein E8-1.8, the Influenza antigens—HA and Neuraminidase and the human HCV related protein CEP and Angioprotein 1 receptor precursor (Tables 1-3).

In one embodiment the signal peptide-derived peptide vaccine comprises the amino acid sequence selected from the group consisting of the amino acid sequences listed in Table 1, SEQ ID NOs: 1-54.

The MHC prediction calculations were adjusted according to dominant Class I and II alleles in populations of various territories. The outcome is MHC-prediction coverage for three main territories: Western population (listed in table 1), Sub Saharan Africa (listed in table 2) and South West Asia (listed in table 3).

According to one specific embodiment, the present invention relates to a peptide vaccine comprising the signal peptide domain of a tuberculosis protein.

Preferably, said peptide is not longer than 40 amino acids.

According to specific embodiments said peptide vaccine comprises at least one amino acid sequence selected from the group consisting of:

```
                                           (SEQ ID NO. 1)
MKIRLHTLLAVLTAAPLLLAAAGCGS designated herein VXL-200;

(SEQ ID NO. 2)
MTDVSRKIRAWGRRLMIGTAAAVVLPGLVGLAGGAATAGA designated herein VXL-201;

(SEQ ID NO. 4)
MKRGLTVAVAGAAILVAGLSGCSS designated herein VXL-203;

(SEQ ID NO. 7)
MKTGTATTRRRLLAVLIALALPGAAVA designated herein VXL-206;

(SEQ ID NO. 8)
MAAMWRRRPLSSALLSFGLLLGGLPLAAPPLAGA designated herein VXL-207;

(SEQ ID NO. 9)
MRFAQPSALSRFSALTRDWFTSTFAAPTAAQA designated herein VXL-208;

(SEQ ID NO. 12)
MLVLLVAVLVTAVYAFVHA designated herein VXL-211;

(SEQ ID NO. 13)
MLLRKGTVYVLVIRADINNAMVAHA designated herein VXL-212;

(SEQ ID NO. 15)
MRPSRYAPLLCAMVLALAWLSAVAG designated herein VXL-214;
```

According to further embodiments said peptide vaccine consists of at least one amino acid sequence selected from the group consisting of: SEQ ID NO. 1, SEQ ID NO. 2, SEQ ID NO. 4, SEQ ID NO. 7, SEQ ID NO. 8, SEQ ID NO. 9, SEQ ID NO. 12, SEQ ID NO. 13, and SEQ ID NO. 15.

In a specific embodiment said peptide vaccine consists of at least one amino acid sequence selected from the group consisting of SEQ ID NO. 2, SEQ ID NO. 4, SEQ ID NO. 9, SEQ ID NO. 12, and SEQ ID NO. 13.

In one embodiment, the peptide vaccine comprises a combination of at least two signal peptides.

In another aspect, the invention encompasses a polypeptide vaccine comprising a recombinant polypeptide comprising at least one signal peptide domain of a target protein of an intracellular pathogen or a pathogen-induced host protein.

In a specific embodiment, the polypeptide vaccine comprises at least two signal peptide domains of target proteins derived from an intracellular pathogen or a pathogen-induced host protein. In a further embodiment said at least two signal peptide domains are selected from the group consisting of SEQ ID NO. 1, SEQ ID NO. 2, SEQ ID NO. 4, SEQ ID NO. 7, SEQ ID NO. 8, SEQ ID NO. 9, SEQ ID NO. 12, SEQ ID NO. 13, and SEQ ID NO. 15. In a further specific embodiment, the polypeptide vaccine comprises at least two signal peptide domains selected from the group consisting of SEQ ID NO. 2, SEQ ID NO. 4, SEQ ID NO. 9, SEQ ID NO. 12, and SEQ ID NO. 13 (corresponding to the peptides VXL201, VXL 203, VXL 208, VXL 211, and VXL 212, respectively). Said polypeptide preferably comprises additional amino acid sequences in between the VXL peptides. Without wishing to be bound by theory, these additional amino acid sequences are intended to reduce the hydrophobicity of the chimeric molecule. In one specific embodiment the ratio between the VXL peptides and the additional amino acid sequences in the chimeric polypeptide is about 1:1.

In one specific embodiment said polypeptide vaccine comprises the amino acid sequence denoted in SEQ ID NO: 55, or an amino acid sequences having at least 85% homology with SEQ ID NO: 55, or an amino acid sequence having at least 90% homology with SEQ ID NO: 55, or an amino acid sequence having at least 95% homology with SEQ ID NO: 55.

In another specific embodiment, said chimeric polypeptide comprises more than one copy of the amino acid sequence of SEQ ID NO. 2, SEQ ID NO. 4, SEQ ID NO. 9, SEQ ID NO. 12, and SEQ ID NO. 13, namely the chimeric polypeptide comprises repetitions of the VXL peptides.

The present invention further encompasses a polynucleotide encoding the chimeric polypeptide, as well as vectors comprising same and host cells comprising said vector or polynucleotide. Said polynucleotide may further comprise at least one restriction site. Such a restriction site may be employed for removing one or more of the VXL peptides from the chimeric polypeptide.

The present invention also concerns use of the peptide vaccines described above in the preparation of pharmaceutical compositions for treating or preventing pathogenic infections.

The invention further concerns pharmaceutical compositions comprising at least one of said peptide vaccines and a pharmaceutically acceptable carrier or diluents, and the use of said peptide vaccines or said pharmaceutical compositions as anti-pathogenic vaccines to treat or prevent infections. In one embodiment said infections are caused by *mycobacterium tuberculosis*.

Optionally, said pharmaceutical compositions further comprise an adjuvant

The present invention also encompasses pharmaceutical compositions comprising a combination of at least two peptide vaccines, thereby allowing vaccination against several different antigens of the same pathogen or against several different pathogens.

The invention further concerns nucleic acid molecules encoding said peptides, and antigen presenting cells (APC), e.g. dendritic cells, presenting said peptides, as well as pharmaceutical compositions comprising said nucleic acid molecules, or said cells.

The invention also concerns use of the peptide vaccines for enrichment of T cell populations in vitro. Thus obtaining a peptide-specific enriched T cell population.

The invention further concerns the use of said nucleic acid molecules, cells, or pharmaceutical compositions comprising same as anti-infective vaccines to treat or prevent pathogenic infections. In one embodiment said infections are caused by *mycobacterium tuberculosis*, or malaria.

Further aspects of the present invention are directed to a method for treating or for preventing infections by administering the pharmaceutical compositions of the present invention to a patient in need thereof.

The pharmaceutical compositions of the invention may be adapted for use in combination with other anti pathogenic agents, for example, antibodies or antibiotics.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 1 is a list of vaccine candidates for Tuberculosis. The amino acid sequence of the vaccine candidates is presented in the right column. The left and mid columns represent internal terminology (VXL) and the respective protein designation.

FIG. 4 is a graphical representation of proliferation responses induced by VXL tuberculosis vaccine candidates on naïve PBMC derived from PPD-positive versus PPD-negative donors. The results are presented as average of direct stimulation index (SI) with SD (A) or as % of positive proliferation response (SI≥2) in PPD positive donors (black box) and PPD negative donors (white box) (B). Results are an average of 8 different experiments, using 11 donors.

FIG. 5 is a table providing characteristics of tuberculosis patients including their ethnic group and disease-associated parameters.

FIG. 7 is a graphical representation of cytokine secretion, as measured by quantitative ELISA, by PBMC obtained from naïve donors. PBMC were stimulated in vitro, using the tuberculosis peptides of the invention for a period of 48 hrs. FIG. 7B represents one of three similar experiments showing cytokine secretion (ng/ml) and proliferation response (as indicated by SI) to stimulation with the most potent VC VXL208 (B1), VXL211 (B2), VXL212 (B3), or VXL203 (B4) in 5 of the 11 donors.

FIG. 8 is a graphical representation of cytokine secretion, as measured by quantitative ELISA, by PBMC obtained from tuberculosis (Mtb) patients. PBMC were stimulated in vitro, using the tuberculosis peptides of the invention for a period of 48 hrs. FIG. 8B demonstrates cytokine secretion (ng/ml) and proliferation response (as indicated by SI) to stimulation with VXL203 (B1), VXL208 (B2), VXL211 (B3), or VXL212 (B4) in 6 tuberculosis patients.

FIG. 13A is a table summarizing the presence or absence of lysis activity of various VXL-peptide specific T cell lines (Anti 201, Anti 203, Anti 208, Anti 211, and Anti 212) obtained from naïve donors and Mtb patients. FIG. 13B is a table summarizing the range of activity in the cytotoxicity assay.

FIG. 14 is a table summarizing the characteristics of four VXL-peptide specific T cell lines (Anti 201, Anti 203, Anti 208, and Anti 211). The table shows the percentage of CD4+ or CD8+ cells which express the effector cell marker $CD44^{high}$ and the effector memory marker $CD62L^{high}$.

FIG. 15 is a schematic representation of FACS analysis results showing the percentage of IFN-gamma production by various peptide specific T cell lines. FIG. 15A—represents data obtained with the VXL203-peptide specific T cell line; FIG. 15B—represents data obtained with the 203A-peptide specific T cell line; FIG. 15C—represents data obtained with the VXL211-peptide specific T cell line; and FIG. 15D—represents data obtained with the 211A-peptide specific T cell line.

DETAILED DESCRIPTION

Figure 2A:
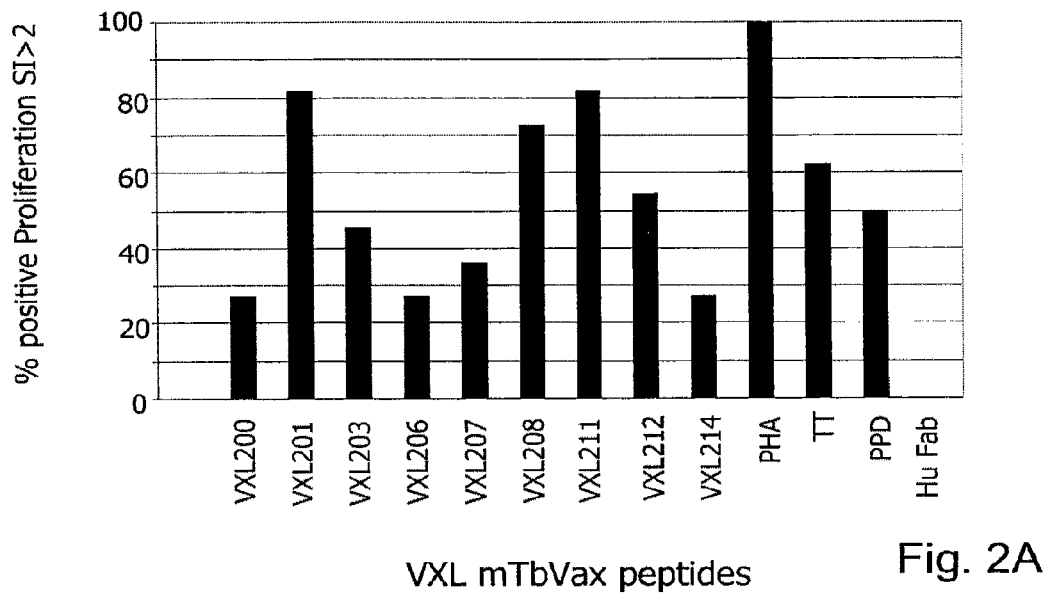
FIG. 2 is a graphical representation of proliferation responses induced by VXL tuberculosis vaccine candidates (VXL) on naïve peripheral blood mononuclear cells (PBMC). Results are indicated as a positive stimulation index SI≥2 (A) or as an average stimulation index (SI) and standard deviation (B). SI was calculated by dividing the CPM (counts per minute) obtained in an analyzed sample to the CPM in a control sample (medium). Results are an average of 8 different experiments using 11 donors. PHA (phetohemaglutinin), TT (tetanus Toxoid) and tuberculosis Purified protein Derivative (PPD) served as positive controls while HuFab (human Fab antibody fragment) was used as a negative control.

The present invention is based on the use of signal peptide sequences as a source for the preparation of promiscuous T cell epitope peptide vaccines with excellent immunodominant properties against intracellular pathogens. The uniqueness of the peptide vaccines of the invention stems from their ability to bind multiple MHC class I and MHC class II alleles. This feature enables the generation of a robust immune response via combined simultaneous activation of both CD4+ and CD8+-restricted T cell clones and coverage of the majority of the population via binding to multiple class I or II alleles, while using a single, relatively short sequence of amino acids. As used herein the term CD4+ or CD8+ refers to cluster of differentiation 4 or 8, respectively.

In addition, and without wishing to be bound by theory, the peptide vaccines of the invention have an internal adjuvant property which elevates their immunodominant properties. Furthermore, said peptide vaccines have TAP independent pathway for entering the ER thereby, they can better deal with the TAP-related immune escape mechanism and consequently with the pathogen's ability to down regulate MHC molecules. Suitable antigens for vaccination in accordance with the invention (hereinafter defined as "target antigens") include two main groups:

A. Pathogen associated antigens: These are antigens which are known or have the potential to be immunogenic and to be expressed by host cells (Target Cells) at a preferred site and time during the process of infection.

B. Host associated antigens: These are antigens which are unregulated and overexpressed by target cell post infection and although considered to be self can induce specific immunity to pathogen infected cells at a preferred site and time during the process of infection.

The present invention provides pathogen specific vaccines which are capable of inducing an effective T-cell response against an intracellular pathogen, and which are based on the signal peptide sequence of proteins associated with the pathogen infection.

It is well known that host defense against intracellular pathogens depends on effective cell-mediated immunity (CMI), in which interactions between T cells and macrophages are crucial. A principal effector mechanism of CMI is through the production of key type I cytokines, particularly interferon-γ, IL-2, and IL-12 which are being produced by antigen-specific activated CD4+ helper T cells, antigen specific CD8+ Cytotoxic T-cells, and antigen presenting cells (APC). Such antigen specific CD8+ Cytotoxic T-cells possess a high lytic capacity for infected cells, and are also capable of eliminating parasites. Such cells also have life-long memory immunity.

It is widely accepted today that protective immunity against tuberculosis relies on the activation of T cells rather than B cells. Within the T cell family, it is the CD4+ T cells which are thought to be important in fending off Mtb. However, CD8+ cells are also known to participate in the anti-Mtb immune response, but their relative importance during the progressive stages of the disease remains elusive. T cells are known to exert their function at least partly through secretion of cytokines. In particular interferon-gamma (IFN-Gamma) and interleukin-12 (IL-12) have been ascribed beneficial roles in protection against TB and exceptional susceptibility to TB has been described in human individuals who are genetically deficient for IFN-Gamma receptor, the IL-12 receptor or IL-12.

In spite of a multitude of treatments against Malaria, around 2 to 3 million lives are still lost every year with approximately 90% of these in Sub-Saharan Africa.

Immunization with radiation-attenuated *Plasmodium* sp. sporozoites1 remains the 'gold standard' for malaria vaccine development; the vaccine prevents both the development of the clinical symptoms of malaria and the transmission of the disease. Nevertheless, despite intense research for decades, the mechanisms and antigenic targets of protective immunity to malaria remain poorly understood.

It is believed today that an efficient protective malaria vaccine needs to elicit a combination of robust CD4+ and CD8+ against key antigens expressed during the early stages of infection i.e. in the draining lymph node and liver. The combination of both effector cells is a key. While Helper CD4 T cells are thought to be a key in fending off *Plasmodium*, the action of effective Cytotoxic T cells that act via cytokine secretion and specific lysis of infected cells (probably hepatocytes) is also critical.

Lymphotropic Herpesviruses (LH), Epstein-Barr Virus (EBV), Cytomegalovirus (CMV), and human Herpesvirus-6 (HHV-6), establish a lifelong persistent infection in most people. They usually produce unapparent infection or transient immune compromise in otherwise healthy hosts but are able to cause life-threatening primary or reactivated infections in individuals with congenital or acquired T-cell immunodeficiency. The spectrum of diseases caused by LH, and CMV is well documented in patients undergoing bone marrow transplantation (BMT) or organ transplantation and in individuals infected with human immunodeficiency virus (HIV). Monitoring of EBV DNA load in the circulation is clinically valuable for the management of EBV-associated diseases, including primary infections in early adulthood which exhibit acute inflammatory diseases known as infectious mononucleosis and chronic forms associated with different Human malignancies such as nasopharyngeal carcinoma (NPC), Gastric carcinoma, and certain lymphomas such as Burkitt's Lymphoma and Hodgkin's disease. CMV is ubiquitous in humans. Around the world the mean seropositivity rate varies with location, race, and socioeconomic status. However in any location, almost all the individuals eventually become infected, ranging from 60-70% in urban U.S. cities to 100% in Africa. The immunosuppressive regimens used for transplanted patients predispose them to CMV disease. Infected organs or blood transfusions are the most common sources of infection. In these patients the severity of the disease is related to the degree of immunosuppression. Morbidity due to donation from a seropositive donor to seronegative recipient is usually higher and manifested as intestinal pneumonia and hepatitis.

Antigen Processing in Eukaryotic Cells

In Eukaryotic cells, protein levels are carefully regulated. Every protein is subject to continuous turnover and degradation. The pathway by which endogenous antigens are degraded for presentation by class I MHC molecules utilizes the same pathways involved in the normal turnover of intracellular proteins. Intracellular proteins are degraded into short peptides by a cytosolic proteolytic multifunctional system called proteasome present in all cells. The proteasome involved in antigen processing includes three subunits LMP2, LMP7 and LMP10.

The peptidase activities of Proteasome containing LMP 2, 7 and 10 generates peptides with preferred binding to MHC class I. The transport of proteasome-degraded peptides into the endoplasmic reticulum (ER) involves an ATP dependent transporter designated TAP. This is a membrane-spanning heterodimer consisting of two proteins TAP1 and TAP2. TAP has a higher affinity to peptide with hydrophobic Amino acids, the preferred anchor residues for MHC class I.

In this regard, signal peptide sequences from self or foreign antigens which are highly hydrophobic are more likely to get a better access to MHC molecules via their preferred binding to TAP1 and TAP2 molecules (Immunology 5$^{th}$ addition R A Goldsby, T J Kindt, B A Osborne and J Kuby).

Since peptide presentation on MHC class I is a key for mounting an effective cellular immunity, intracellular pathogens are constantly trying to abrogate this machinery. One mechanism for achieving this goal is via specific mutation in the TAP transporter. Practically, TAP1 or TAP2 mutations halt the MHC peptide interaction in the ER leading to limited presentation of MHC-peptide complexes on the cell membrane. As will be explained in the next paragraph, SP sequences are the only peptides which deal with these mutations as they have a TAP-independent pathway for penetrating into the ER.

Signal Peptide Processing

In both bacteria (prokaryotic) and eukaryotic cells, proteins destined for secretion or for insertion into cellular membranes need to be targeted appropriately. Genes that encode such proteins specify a short, amino-terminal signal peptide (termed also signal sequence) that is required for the protein to find its way to the membrane. Although all signal peptides have a common motif, there is no homology between signal peptides in different proteins. The signal peptide is proteolytically removed in the ER after its targeting role has been performed. In both types of organisms, a signal recognition particle (SRP) is responsible for recognizing and binding to a signal peptide sequence at the amino terminus of a growing, membrane-bound protein. The SRP then targets the ribosome that is synthesizing the protein to either the endoplasmic reticulum (ER) in eukaryotes, or to the bacteria plasma membrane in bacteria. The SRP binds to ribosomes at the site of the exit tunnel and interacts with the N-terminal end of newly synthesized protein. If the protein contains a SP sequence then protein synthesis is temporarily arrested. The complex is directed to the membrane surface and the end of the protein is inserted through a pore in the membrane. Protein synthesis then continues and the newly synthesized protein is inserted into the endoplasmic reticulum in eukaryotes or across the plasma membrane in bacteria. In the final step a SP specific peptidase is releasing the SP into the lumen of the ER where it can bind MHC molecules. This is a normal process which runs in parallel to the proteasome machinery. Moreover, it was well demonstrated in various reports that SP linked to short sequences and even isolated SP per se (without the entire protein chain), can penetrate the ER via the same specific peptidase.

The mechanisms of antigen presentation for proteins derived from intracellular bacteria are more complicated since these proteins presumably need to first reach the host cytosol and only than penetrate into the host's ER for MHC presentation. There is limited information about this process but there is sufficient evidence for CTL activity against key epitopes in bacteria. Potential mechanisms are the following:

1. Phagosome: Intracellular organelles which lyse bacteria and transport the processed antigen for direct presentation on MHC.
2. Bacteria secreted protein (having bacteria SP sequences), can be degraded in the cytosol by the proteasome and enter the ER via the TAP machinery.
3. SP sequences from Bacteria having also the binding motif of the human SP peptidase can, as explained above, penetrate independently the ER. This is a proteasome independent mechanism that can potentially also in the absent of functional TAP transporter.

Selection of the Vaccine Candidate

The present invention provides signal peptide (SP)-based vaccine candidates against intracellular pathogens. Such vaccines may be preventive or therapeutic vaccines.

Such intracellular pathogens include, but are not limited to bacteria, Mtb. Antigenic targets for development of an anti-pathogen vaccine can be selected based on any desired criteria, for example, using the following key parameters:

Pathogen or host antigens which are differentially expressed in pathogen-infected cells (Host Cells).

Eligible targets for an immune assault

Predicted as binding for class I, and II (and therefore likely to be immunogenic) in the majority of the population; and Having less than 80% homology with any self (human host) antigen.

Preferably such targets are expressed at a preferred site and time during the process of infection, e.g. in the case of Mtb infection in the human Lung and lymph nodes or in the case of Malaria infection in the human liver or spleen.

Searching for a Comprehensive List of Eligible Target Proteins

Several information sources can be used for selection of relevant target proteins, for example: Published scientific articles, patents or patent applications; sequence databases such as Blast or uniprot search; a signal peptide database website which provides a direct access to the signal sequence domain of Mammals, *Drosophila*, Bacteria and Viruses (http://www.signalpeptide.de/index.php?m=listspdb); and a list of published epitope antigens in the website of Immune Epitope Database and Analysis Resource (IEDB).

Checking the List for Eligible Targets for an Immune Assault

Each protein was checked for eligibility to become an immune target according to the criteria defined above.

Proteins with the following attributes were removed from the list:

1. Host proteins that are sub-cellularly located in organelles or in localization that does not require transport from the ER-Golgi, and thus have no signal peptides (e.g. purely cytoplasmic proteins (e.g. ATP-citrate synthase)).
2. Host proteins that are ubiquitously expressed in many tissues (e.g. TUBB, RBM4).
3. Immune-related proteins (e.g. PSME2, CD213a2, M-CSF).
4. Proteins which are expressed in cells which do not have MHC presentation (i.e. RBC).

Identifying the Signal Peptides (SP)

Proteins that were eligible targets for an immune assault were checked for the presence of a signal peptide. The SignalP 3.0 program was used to determine the signal peptide sequence (http://www.cbs.dtu.dk/services/SignalP/). Information was also confirmed for SP sequences isolated in other websites e.g. "The signal peptide database". The program uses both a neural network (NN) algorithm and a Hidden Markov models (HMM) algorithm. A sequence was considered to be a signal peptide whenever a score of over 0.3 was received in one or more of the algorithms. In the case of bacterial antigens, targets were evaluated for the presence of bacterial SP and human SP. In addition, the human SP was required to be smaller in size from the bacterial SP.

Checking for Predicted Binding of Predicted Peptides

To check whether peptides from the 17-40 amino acid signal peptides bind to frequently appearing human leukocyte antigen (HLA) haplotypes, we collected information on HLA allele frequency from the dbMHC site belonging to the ncbi.

First, the alleles of HLA class I (HLA-A, B, C), and HLA class II (HLA-DRB1) which appear most frequently in a selected population were determined. Online prediction programs that were used:
1. BIMAS: used for most of the predictions for HLA class I alleles.
2. NetMHC: used for the prediction of certain HLA class I alleles which are more frequent in selected populations e.g. South West Asia and Sub Sahara Africa. This software uses for certain alleles the Neuronal network prediction methodology and for other alleles the Scoring Matrix methodology.
3. Propred: used to predict most DRB1 genotypes.
4. Immune Epitope: used for the prediction of the HLA-DRB1-0901 genotype that is not predicted by Propred.

Defining Differential Strength of Binding

In each of the programs used, various differential strengths of binding were defined:
1. BIMAS: Strong=peptide score of 100+, Medium=10-100, Weak=5-10.
2. NetMHC: for neuronal network Strong=peptide score of 1-50, Medium=50-500, Weak=500-5000 nM. For scoring matrix there is a specific threshold score given for each allele. Nevertheless, the threshold was always in the following range, Strong=peptide score in the range of above 12.5-15 Weak=1-8.5, Medium=was in the range of 8.5-(12.5-15) depending on the allele.
3. Propred: Strong=top 1% of binders, Medium=1-2% of binders, Weak=2-3% of binders
4. Immune Epitope: Strong=$IC_{50}$ of 0.01 nM-10 nM, Medium=10-100 nM, Weak=100-10,000 nM
5. MHC2Pred: Strong=cutoff 1.0, medium=cutoff 0.5, Weak=cutoff 0. As serotype prediction is expected to be less accurate than genotype prediction, only high and medium binders were predicted with MHC2Pred.

Determining the Predicted Percentage of Population that has Alleles that have Predicted Binding Peptides within a Specific Signal Peptide To calculate the probability that a patient (or a population) has one or more alleles predicted to bind a certain signal peptide, a statistic calculation using complementary probabilities was used. Independent distribution of alleles in the population was assumed.

Calculation: if peptide X was predicted as a peptide that binds to only four HLA-class I alleles: HLA-A1 (frequency 0.1), HLA-B2 (freq.=0.2), HLA-B3 (freq.=0.3), and HLA-C4 (freq. 0.4) then the probability that it would bind neither of these alleles is the product of the probabilities that it would bind neither HLA-A1 (1-0.1), nor HLA-B2 (1-0.2), nor HLA-B3 (1-0.3), nor HLA-C4 (1-0.4) therefore the probability is:

$$(1-0.1)(1-0.2)(1-0.3)(1-0.4)=0.3024.$$

The probability that the patient has one or more of the binding alleles is 1 minus the probability that he would have none of the binding alleles:

$$1-0.3024=0.6976$$

The calculation was done separately for the HLA class I alleles, the HLA-class II alleles (genotypes), and the HLA class II alleles (serotypes). Each list contained no overlapping alleles (e.g. HLA-A02 and HLA-A0201).

Peptides that would bind in the majority (>50%) of the population (both in the HLA class I and in the HLA class II alleles) were further followed.

Table 1 provides a comprehensive list of selected targets suitable for addressing the Western population with respect to Class I and Class II allele coverage.

TABLE 1

| SEQ. No. | Protein | Disease | length | SP sequence | % MHC-I | % MHC-II |
|---|---|---|---|---|---|---|
| 1 | BPBP1 | Tuberculosis | 26 | MKIRLHTLLA VLTAAPLLLA AAGCGS | 75 | 52 |
| 2 | Antigen 85B | Tuberculosis | 40 | MTDVSRKIRA WGRRLMIGTA AAWLPGLVG LAGGAATAGA | 85 | 52 |
| 3 | Antigen 85B-Precursor | leprae | 38 | MIDVSGKIRA WGRWLLVGAA ATLPSLISLA GGAATASA | 82 | 36 |
| 4 | Lipoprotein IpqH | Tuberculosis | 24 | MKRGLTVAVA GAAILVAGLS GCSS | 86 | 52 |
| 5 | Putative lipoprotein (Possible lipoprotein) | leprae | 20 | MRHKLLAAIY AVTIMAGAAG CSGGTQA | 66 | 45 |
| 6 | Beta gluconase putative | Tuberculosis | 31 | MLMPEMDRRR MMMMAGFGAL AAALPAPTAW A | 85 | 41 |
| 7 | Hypothetical protein MT0 213 | Tuberculosis | 27 | MKTGTATTRR RLLAVLIALA LPGAAVA | 83 | 48 |
| 8 | Protease | Tuberculosis | 34 | MAAMWRRRPL SSALLSFGLL LGGLPLAAPP LAGA | 81 | 41 |
| 9 | ATP dependet helicase putative | Tuberculosis | 32 | MRFAQPSALS RFSALTRDWF TSTFAAPTAA QA | 84 | 37 |
| 10 | Hypotethical protein MT1221 | Tuberculosis | 37 | MLSRTRFSMQ RQMKRVIAGA FAVWLVGWAG GFGTAIA | 61 | 41 |
| 11 | BCG | Tuberculosis | 23 | MRIKIFMLVT AVVLLCCSGV ATA | 69 | 52 |
| 12 | Un char protein Rv0476/MTO4941 prec | Tuberculosis | 19 | MLVLLAVLVTAVYAFVHA | 84 | 50 |
| 13 | Un char protein Rv1334/MT1376 prec | Tuberculosis | 20 | MLLRKGTVYVLVIRADLVNAMVAHA | 79 | 50 |

TABLE 1-continued

| SEQ. No. | Protein | Disease | length | SP sequence | % MHC-I | % MHC-II |
|---|---|---|---|---|---|---|
| 14 | Putative lipoprotein IprB prec | Tuberculosis | 24 | MRRKVRRLTLAVSALVALFPAVAG | 71 | 50 |
| 15 | Putative lipoprotein IpqV prec | Tuberculosis | 25 | MRPSRYAPLLCAMVLALAWLSAVAG | 83 | 47 |
| 16 | Beta-Lactomase precursor | Tuberculosis | 30 | MRNRGFGRRELLVAMAMLVSVTGCARHASG | 81 | 43 |
| 17 | Circumsporozoit protein precursor | P. Falciparum | 18 | MMRKLAILSV SSFLFVEA | 74 | 52 |
| 18 | Malaria exported protein-1 | P. Falciparum | 22 | MKILSVFFLV LFFIIFNKES LA | 86 | 52 |
| 19 | Liver stage antigen (LSA-1) | P. Falciparum | 23 | MKHILYISFY FILVNLLIFH ING | 84 | 52 |
| 20 | Sporozoit surface antigen 2 | P. Falciparum | 25 | MNHLGNVKYL VIVFLIFFDL FLVNG | 84 | 52 |
| 21 | MSP1 (merozoit surface protein 1 precur) | P. Falciparum | 20 | MKIIFFLCSF LFFIINTQCV | 82 | 52 |
| 22 | Protein Antigen | P. Falciparum | 25 | MNIRKFIPSL ALMLIFFAFA NLVLS | 85 | 45 |
| 23 | Cytoadherence linked asexual protein, CLAG | P. Vivax | 24 | MTSLRNMRVF FLFVLLFISK NVIG | 79 | 52 |
| 24 | Membrane protein PF12 | P. Vivax | 23 | MRIAKAALCG QLLIWWLSAP AEG | 78 | 45 |
| 25 | Exported protein 2, putative | P. Vivax | 21 | MKVSYILSLF FFLITYKNTT T | 83 | 48 |
| 26 | Circumsporozoite-protein related antigen | P. Vivax | 21 | MKLLAAVFLL FCAILCNHAL G | 75 | 41 |
| 27 | Circumsporozoite protein precursor | P. Vivax | 22 | MKNFILLAVS SILLVDLFPT HC | 78 | 52 |
| 28 | Merozoite surface protein 3 alfa | P. Vivax | 23 | MKHTRSVTLY LFLLTLCAYL TGA | 84 | 43 |
| 29 | CTRP adhesive protein invasiv stage | P. Vivax | 23 | MNKSFLLIAS YFCLVVHLGT VIA | 82 | 52 |
| 30 | GRA-1 | Toxoplasma gondii | 24 | MVRVSAIVGA AASVFVCLSA GAYA | 75 | 48 |
| 31 | SAG1 | Toxoplasma gondii | 39 | MSVSLHHFII SSGFLTSMFP KAVRRAVTAG VFAAPTLMS | 80 | 45 |
| 32 | Surface antigen SAG1 | Toxoplasma gondii | 30 | MFPKAVRRAV TAGVFAAPTL MSFLLCGVMA | 87 | 45 |
| 33 | Surface Antigen P22 | Toxoplasma gondii | 26 | MSFSKTTSLA SLALTGLFVV FQFALA | 82 | 41 |
| 34 | Rhoptry protein 10 | Toxoplasma gondii | 28 | MGRPRWPLPS MFFLSLLCVS EKRFSVSG | 85 | 45 |
| 35 | Glycoprotein GP85 | EBV | 17 | MQLLCVFCLV LLWEVGA | 71 | 52 |
| 36 | BCRF-1 | EBV | 23 | MERRLVVTLQ CLVLLYLAPE CGG | 87 | 52 |
| 37 | Glycoprotein B | CMV | 25 | MESRIWCLVV CVNLCIVCLG AAVSS | 75 | 52 |
| 38 | Retinoic acid early inducible gene-1 (RAE-1) | CMV, NH1 | 30 | MRRISLTSSP VRLLLFLLLL LIALEIMYNS | 86 | 52 |
| 39 | Unique short US8 glycoprotein precursor | CMV | 21 | MRRWLRLLVG LGCCWVTLAH A | 69 | 45 |
| 40 | US9 Protein | CMV Human herpesvirus 5) | 27 | MILWSPSTCS FFWHWCLIAV SVLSSRS | 63 | 45 |
| 41 | Unique short US7 glycoprotein precursor | CMV Human herpesvirus 5 (HHV5) | 27 | MRIQLLLVAT LVASIVATRV EDMATFR | 80 | 52 |
| 42 | Hu PrP | Viroid/Hibatitis | 22 | MANLGCWMLV LFVATWSDLG LC | 76 | 52 |
| 43 | Envelop Glycoprotein | HIV | 30 | MRVKEKYQHL WRWGWKWGTM LLGILMICSA | 81 | 45 |
| 44 | Hu reticulocalbin-2 precursor | HIV | 25 | MRLGPRTAAL GLLLLCAAAA GAGKA | 82 | 41 |

TABLE 1-continued

| SEQ. No. | Protein | Disease | length | SP sequence | % MHC-I | % MHC-II |
|---|---|---|---|---|---|---|
| 45 | Hu neuronalacetycholine reccep. alfa 3 | HIV | 29 | MALAVSLPLA LSPPRLLLLL LSLLPVARA | 84 | 52 |
| 46 | Envel polyprotein GP '160 precursor | HIV | 29 | MRATEIRKNY QHLWKGGTLL LGMLMICSA | 85 | 41 |
| 47 | Envel Protein GP160 precursor | HIV | 29 | MRVKGIRRNY QHWWGWGTML LGLLMICSA | 80 | 45 |
| 48 | Transforming membrane receptor-like protein. | HIV HHV-8 | 18 | MLLCIVCSLL VCFPKLLS | 69 | 48 |
| 49 | HHV-8 glycoprotein E8-1.8 | HV8 | 26 | MSSTQIRTEI PVALLILCLC LVACHA | 83 | 52 |
| 50 | Angioprotein 1 receptor precursor | HCV | 22 | MDSLASLVLC GVSLLLSGTV EG | 71 | 52 |
| 51 | C-Reactive protein | HCV HIV | 18 | MEKLLCFLVL TSLSHAFG | 67 | 45 |
| 52 | Hemagglutenin precursor | NH1 | 17 | MKANLLVLLC ALAAADA | 75 | 45 |
| 53 | Hrmagglutenin precursor | NH1 | 16 | MKTTIILILL THWVYS | 73 | 43 |
| 54 | Neuraminidase | | 26 | MLPSTVQTLT LLLTSGGVLL SLYVSA | 83 | 48 |

Adjusting the Selected MHC Alleles Repertoires to the Eligible Targets/Indications Since the evaluated antigens of the invention emerge from pathogens that are more frequent in certain geographic territories, the MHC prediction calculations were adjusted with dominant Class I and II alleles from these territories. The outcome is MHC-predictions coverage for two main territories: Sub Sahara Africa and South West Asia (in addition to the Western population) for the same list of selected targets.

Tables 2 and 3 provide unique allele coverage for TB and malaria targets suitable for the population in South-West Asia (Table 2) and Sub Saharan Africa (Table 3).

TABLE 2

| | Protein | Disease | length | % MHC-I | % MHC-II |
|---|---|---|---|---|---|
| 1 | BPBP1 | Tuberculosis | 26 | 78 | 66 |
| 2 | Antigen 85B | Tuberculosis | 40 | 77 | 62 |
| 3 | Antigen 85B- Precursor | leprae | 38 | 78 | 49 |
| 4 | Lipoprotein IpqH | Tuberculosis | 24 | 77 | 51 |
| 5 | Lipoprotein LpqH 19 KDa | leprae | 20 | 60 | 56 |
| 6 | Beta gluconase putative | Tuberculosis | 31 | 81 | 57 |
| 7 | Hypothetical protein MT0 213 | Tuberculosis | 27 | 80 | 58 |
| 8 | Protease | Tuberculosis | 34 | 84 | 55 |
| 9 | ATP dependet helicase putative | Tuberculosis | 32 | 81 | 47 |
| 10 | Hypotethical protein MT1221 | Tuberculosis | 37 | 76 | 52 |
| 11 | BCG | Tuberculosis | 23 | 71 | 66 |
| 12 | Un char protein Rv0476/MTO4941 prec | Tuberculosis | 19 | 85 | 62 |
| 13 | Un char protein Rv1334/MT1376 prec | Tuberculosis | 20 | 82 | 66 |
| 14 | Putative lipoprotein IprB prec | Tuberculosis | 25 | 67 | 62 |
| 15 | Putative lipoprotein IpqV prec | Tuberculosis | 25 | 78 | 62 |
| 16 | Beta-Lactomase precursor | Tuberculosis | 30 | 74 | 57 |
| 17 | Circumsporozoit protein precursor | P. Falciparum | 18 | 62 | 66 |
| 18 | Malaria exported protein-1 | P. Falciparum | 22 | 85 | 66 |
| 19 | Liver stage antigen (LSA-1) | P. Falciparum | 23 | 84 | 66 |
| 20 | Sporozoit surface antigen 2 | P. Falciparum | 25 | 80 | 66 |
| 21 | MSP1 (merozoit surface protein 1 precur). | P. Falciparum | 20 | 84 | 62 |
| 22 | Protein Antigen | P. Falciparum | 25 | 80 | 57 |
| 23 | Cytoadherence linked asexual protein, CLAG | P. Vivax | 24 | 78 | 66 |
| 24 | Membrane protein PF12 | P. Vivax | 23 | 78 | 54 |
| 25 | Exported protein 2, putative | P. Vivax | 21 | 83 | 60 |
| 26 | Circumsporozoite-protein related antigen, | P. Vivax | 21 | 77 | 50 |
| 27 | Circumsporozoite protein precursor | P. Vivax | 22 | 76 | 66 |
| 28 | Merozoite surface protein 3 alfa | P. Vivax | 23 | 79 | 57 |
| 29 | CTRP adhesive protein invasiv stage | P. Vivax | 23 | 78 | 66 |

TABLE 3

|   | Name | Source | MHC-I | | MHC-II |
|---|------|--------|-------|---|--------|
| 1 | BPBP1 | Tuberculosis | 26 | 80 | 55 |
| 2 | Antigen 85B | Tuberculosis | 40 | 83 | 62 |
| 3 | Antigen 85B- Precursor | leprae | 38 | 85 | 51 |
| 4 | Lipoprotein IpqH | Tuberculosis | 24 | 86 | 55 |
| 5 | Lipoprotein LpqH 19 KDa | leprae | 20 | 83 | 62 |
| 6 | Beta gluconase putative | Tuberculosis | 31 | 89 | 56 |
| 7 | Hypothetical protein MT0 213 | Tuberculosis | 27 | 86 | 62 |
| 8 | Protease | Tuberculosis | 34 | 81 | 52 |
| 9 | ATP dependet helicase putative | Tuberculosis | 32 | 88 | 30 |
| 10 | Hypotethical protein MT1221 | Tuberculosis | 37 | 89 | 56 |
| 11 | BCG | Tuberculosis | 23 | 74 | 62 |
| 12 | Un char protein Rv0476/MTO4941 prec | Tuberculosis | 19 | 90 | 62 |
| 13 | Un char protein Rv1334/MT1376 prec | Tuberculosis | 20 | 90 | 62 |
| 14 | Putative lipoprotein IprB prec | Tuberculosis | 25 | 84 | 62 |
| 15 | Putative lipoprotein IpqV prec | Tuberculosis | 25 | 91 | 62 |
| 16 | Beta-Lactomase precursor | Tuberculosis | 30 | 84 | 56 |
| 17 | Circumsporozoit protein precursor | P. Falciparum | 18 | 89 | 62 |
| 18 | Malaria exported protein-1 | P. Falciparum | 22 | 92 | 62 |
| 19 | Liver stage antigen (LSA-1) | P. Falciparum | 23 | 93 | 62 |
| 20 | Sporozoit surface antigen 2 | P. Falciparum | 25 | 92 | 62 |
| 21 | MSP1 (merozoit surface protein 1 precur). | P. Falciparum | 20 | 90 | 62 |
| 22 | Protein Antigen | P. Falciparum | 25 | 94 | 56 |
| 23 | Cytoadherence linked asexual protein, CLAG | P. Vivax | 24 | 91 | 62 |
| 24 | Membrane protein PF12 | P. Vivax | 23 | 83 | 57 |
| 25 | Exported protein 2, putative | P. Vivax | 21 | 91 | 62 |
| 26 | Circumsporozoite-protein related antigen, | P. Vivax | 21 | 82 | 49 |
| 27 | Circumsporozoite protein precursor | P. Vivax | 22 | 81 | 55 |
| 28 | Merozoite surface protein 3 alfa | P. Vivax | 23 | 89 | 56 |
| 29 | CTRP adhesive protein invasiv stage | P. Vivax | 23 | 91 | 62 |

Determining the Percentage of Homology Between a Selected Antigen with a Specific Signal Peptide and Other Self Proteins The selected putative SP Antigens were then evaluated for homology with human proteins using Genbank http://www.ncbi.nlm.nih.gov:80/blast/. Though most of the selected SP antigens did not show identity with human sequences, any peptide which shared greater than 80% identity with peptides contained in the human genome would have been considered for elimination prior to selection for synthesis. Practically, similarity was searched in the minimal class 19mer epitopes.

Preferred antigens in accordance with the invention are listed in Tables 1-3, in particular:

1. TB derived antigens, "Putative lipoprotein lpqV precursor" (VXL214) "BPBP1" (VXL200), Hypothetical protein MTO 213 (VXL206), Protease (VXL207), having an SP of 25, 26, 27 and 34 AA long respectively, high SP score, over 50% binding for both class I and II and no homology with human sequences. Additional preferred TB antigens are provided in FIG. 1. Specifically those antigens denoted as ATP dependent Helicase putative (VXL208), Uncharacterized protein Rv0476/MT04941 precursor (VXL211), Uncharacterized protein Rv1334/MT1376 precursor (VXL212), Antigen 85B (VXL201) and "Lipoprotein lpqH (VXL203).
2. The Malaria antigens "exported protein-1", "Sporozoit surface antigen 2" and "MSP1" which are less than 25 AA long, have a high SP score, over 50% for both class I and II and no homology with human sequences.
3. The *Toxoplasma* "GRA-1" antigen.
4. The HCV antigen "Unique short US7 glycoprotein precursor"
5. The HIV "Transforming membrane receptor-like protein" antigen
6. Influenza Hemagglutinin precursor and Neuraminidase Evaluation of the Selected Candidates In Vitro Analysis Signal peptide vaccine candidates (VCs) that were selected according to the above criteria were synthesized and partially purified (>70% purity) for initial evaluation. The evaluation process included in vitro experiments for determination of immune properties as follows: peripheral blood mononuclear cells (PBMCs) were obtained from a large pool of healthy (PPD positive and Negative) and infected donors, e.g. individuals with active Mtb, and stimulated with the selected multi-epitope VCs. The stimulated PCMCs were subjected to proliferation assays evaluating three main parameters; absolute stimulation index (SI), percentage of positive SI≥2 stimulations and key cytokine secretion, primarily IFN-Gamma, IL-2, IL-4 and IL-12 as measured in an ELISA assay.

Peptide VCs which tested positive in the above assays were further purified (>90% purity) and subjected to further development. Additional experiments included comparing the activity of the pure SP-derived VCs to that of other antigen-matched epitopes derived from other domains. Separately, T cell lines directed against the most potent immunodominant multi-epitope VCs, in accordance with the invention, were established from naïve and infected donors, and the T cell phenotype and function were examined.

For phenotype characterization, these T cell lines were evaluated in FACS analysis for the following cell surface markers: CD3, CD4, CD8, CD45RO, CD44, and CD62L.

For functional characterization, these T cell lines were further evaluated in several cytotoxicity assays. In these studies, target cells were either autologous human macrophages loaded with one of the multi-epitope VCs or autologous macrophages infected with a live pathogen (e.g. Mtb).

Functional properties of the same T cell lines were also manifested in FACS analysis measuring in an Intra-Cellular staining (ICS) assay IFN-Gamma and IL-4 levels in CD4, and CD8 cells. This assay specifically determines the phenotype of the vaccine-reacting T cells subpopulations. IFN-Gamma, IL-2, IL-4 and IL-12 cytokine secretion levels were also measured in the same T cell lines using ELISA assay either during the process of generating the T cell line or during the lysis process to confirm a correlation between strong lysis and high IFN-Gamma secretion of the effector cells.

Constructing a Multi-Antigenic and Multi-Epitopes Recombinant Protein Containing the Most Potent VCs mTbuVax is an artificial recombinant protein vaccine containing the five most immunodominant multi-epitope VCs VXL201, VXL203, VXL208, VXL211 and VXL212 separated by flexible linkers. In addition, 5-7 different restriction sites were also designed in the construct to enables simple extension of the linker and replacement of the VCs along the gene. Briefly, the designed gene was synthetically synthesized, introduced into a plasmid, propagated and sequenced in order to verify the required sequence. The amino acid sequence of the recombinant protein is as follows (SEQ ID NO: 55):

TMGSGGSGASGGSGKKKKKKKMLLRKGTVYVLVIRADLVNAMVAHAKKK

GGSGASGGSGGASGASGGSGKKKKKKKKMLVLLVAVLVTAVYAFVHAKK

KGGSGASGGSGGGSGASGGSGGGSGSGGGKKKKKKKKMRFAQPSALSRF

SALTRDWFTSTFAAPTAAQAKKKGGSGASGGSGGGSGASGVDTSGSGGSG

GGSGGKKKKKKKKMKRGLTVAVAGAAILVAGLSGCSSKKKGGSGGSGGG

GSGASGGSGGGSGASGGSGGGSGASGGSGKKKKKKKKMTDVSRKIRAWG

RRLMIGTAAAVVLPGLVGLAGGAATAGALE

The nucleic acid sequence of the recombinant protein is as follows (SEQ ID NO: 56):

CCATGGgtagtggcggatctggcgcgagtggcgggagtgggaaaaaga aaaaagaaaaagaaaATGCTGTTACGTAAAGGCACCGTTTATGTGCTGG TCATTCGCGCCGATCTTGTGAATGCGATGGTTGCACATGCGaaaaagaaa ggtggcagtggtgcctctggaggttctgggggtGCTAGCggcgcgagtgg tgggagcgggaagaaaaaaaagaaaaagaaaaagaaaATGCTTGTGCTGC TCGTTGCGGTTCTGGTGACCGCCGTCTACGCATTTGTCCATGCGaaaaag aaaggtggctcaggagccagtggtggaagcgggggtggctccggggcgag cggtggatctggcggagggtctggcagcggcggtgggaaaagaagaaaa aaaagaaaaagaaaATGCGTTTCGCACAGCCGAGCGCGCTGTCTCGCTTT

AGTGCACTGACCCGTGATTGGTTTACGAGCACCTTCGCCGCGCCGACTGC

GGCACAGGCTaagaaaaaaggcggttctggggcgtcaggcgggagcggcg gaggatcaggtgcctctggtGTCGACACTAGTggcagtggagggtctggt ggaggctctggtggcaaaaaaaagaaaaagaaaaagaaaaagATGAAACG

TGGCCTGACCGTTGCGGTGGCAGGTGCGGCCATTCTGGTGGCAGGTCTGA

GCGGCTGCTCTAGTaagaaaaaaggagggagcggcggttcgggcggtgga gggagcggtgcctctggcggttcaggtggcggaagtggggcatccggcgg ttccggcggtggaagcggtgcctctggaggcagtggtaagaaaaagaaaa agaaaaaaagaaaATGACCGATGTTAGCCGCAAAATCCGTGCCTGGGGC

CGTCGCCTGATGATCGGCACCGCAGCTGCGGTTGTGCTGCCGGGTCTGGT

TGGCCTTGCAGGTGGCGCCGCGACCGCAGGCGCGCTCGAG

For expression and optimization, the gene in pET plasmid was introduced into *E. coli* BL21 and expression of the mTbuVax protein was optimized under different growing conditions. Analysis includes SDS-PAGE, affinity purification according to the tag in use and specific anti-VXL sera obtained from TB patients.

In Vivo Evaluation of Immunodominant and Protection Properties

Immunodominant properties of selected vaccine candidates are verified in vivo (in particular CTL development, proliferation) in suitable mice strains, e.g. BALB/C mice, following ex vivo cytotoxicity assessments.

Additional characteristics can be evaluated in protective experiments in Mtb infected mice rescued by adoptive transfer of PBLs activated ex vivo with one or more of the vaccines candidate; or in protective experiments in Mtb infected mice immunized with vaccines candidates.

Furthermore, toxicology studies can be performed in appropriate species for the selected candidate vaccines.

Terms and Definitions

The nomenclature used to describe peptide and/or polynucleotide compounds of the invention follows the conventional practice wherein the amino group (N-terminus) and/or the 5' are presented to the left and the carboxyl group (C-terminus) and/or 3' is presented to the right.

As used herein, the term "peptide vaccine" refers to a preparation composed of at least one peptide that improves immunity to a particular pathogen.

As used herein, the term "peptide" refers to a molecular chain of amino acids, which, if required, can be modified in vivo or in vitro, for example by manosylation, glycosylation, amidation (specifically C-terminal amides), carboxylation or phosphorylation with the stipulation that these modifications must preserve the biological activity of the original molecule. In addition, peptides can be part of a chimeric protein.

Functional derivatives of the peptides are also included in the present invention. Functional derivatives are meant to include peptides which differ in one or more amino acids in the overall sequence, which have deletions, substitutions, inversions or additions. Amino acid substitutions which can be expected not to essentially alter biological and immunological activities have been described. Amino acid replacements between related amino acids or replacements which have occurred frequently in evolution include, inter alia Ser/Ala, Ser/Gly, Asp/Gly, Asp/Asn, Ile/Val.

The peptides according to the invention can be produced synthetically or by recombinant DNA technology. Methods for producing synthetic peptides are well known in the art.

The organic chemical methods for peptide synthesis are considered to include the coupling of the required amino acids by means of a condensation reaction, either in homogenous phase or with the aid of a so-called solid phase. The condensation reaction can be carried out as follows:

Condensation of a compound (amino acid, peptide) with a free carboxyl group and protected other reactive groups with a compound (amino acid, peptide) with a free amino group and protected other reactive groups, in the presence of a condensation agent;

Condensation of a compound (amino acid, peptide) with an activated carboxyl group and free or protected other reaction groups with a compound (amino acid, peptide) with a free amino group and free or protected other reactive groups.

Activation of the carboxyl group can take place, inter alia, by converting the carboxyl group to an acid halide, azide, anhydride, imidazolide or an activated ester, such as the N-hydroxy-succinimide, N-hydroxy-benzotriazole or p-nitrophenyl ester.

In one specific embodiment an amide group is added at the 3' end of the synthetic peptides of the invention.

The most common methods for the above condensation reactions are: the carbodiimide method, the azide method, the mixed anhydride method and the method using activated esters, such as described in The Peptides, Analysis, Synthesis, Biology Vol. 1-3 (Ed. Gross, E. and Meienhofer, J.) 1979, 1980, 1981 (Academic Press, Inc.).

Production of peptides by recombinant DNA techniques is a general method well known in the art. The polypeptide to be expressed is coded for by a nucleic acid sequence.

Also part of the invention is the nucleic acid sequence comprising the sequence encoding the peptides according to the present invention.

As is well known in the art, the degeneracy of the genetic code permits substitution of bases in a codon to result in another codon still coding for the same amino acid, e.g., the codon for the amino acid glutamic acid is both GAT and GAA. Consequently, it is clear that for the expression of a polypeptide with an amino acid sequence as shown in any of SEQ ID NO: 1-9 use can be made of a derivate nucleic acid sequence with such an alternative codon composition thereby different nucleic acid sequences can be used.

The term "Nucleotide sequence" as used herein refers to a polymeric form of nucleotides of any length, both to ribonucleic acid (RNA) sequences and to deoxyribonucleic acid (DNA) sequences. In principle, this term refers to the primary structure of the molecule. Thus, this term includes double and single stranded DNA, as well as double and single stranded RNA, and modifications thereof.

The nucleotide sequences encoding the peptide vaccines of the invention can be used for the production of the peptides using recombinant DNA techniques. For this, the nucleotide sequence must be comprised in a cloning vehicle which can be used to transform or transfect a suitable host cell.

A wide variety of host cell and cloning vehicle combinations may be usefully employed in cloning the nucleic acid sequence. For example, useful cloning vehicles may include chromosomal, non-chromosomal and synthetic DNA sequences such as various known bacterial plasmids, and wider host range plasmids such as pBR 322, the various pUC, pGEM and pBluescript plasmids, bacteriophages, e.g. lambda-gt-Wes, Charon 28 and the M13 derived phages and vectors derived from combinations of plasmids and phage or virus DNA, such as SV40, adenovirus or polyoma virus DNA.

Useful hosts may include bacterial hosts, yeasts and other fungi, plant or animal hosts, such as Chinese Hamster Ovary (CHO) cells, melanoma cells, dendritic cells, monkey cells and other hosts.

Vehicles for use in expression of the peptides may further comprise control sequences operably linked to the nucleic acid sequence coding for the peptide. Such control sequences generally comprise a promoter sequence and sequences which regulate and/or enhance expression levels. Furthermore, an origin of replication and/or a dominant selection marker are often present in such vehicles. Of course, control and other sequences can vary depending on the host cell selected.

Techniques for transforming or transfecting host cells are well known in the art (for instance, Maniatis et al., 1982/1989, Molecular cloning: A laboratory Manual, Cold Spring Harbor Lab.).

The present invention also provides a polynucleotide encoding the signal peptide vaccine of the invention as part of a pharmaceutical composition for targeted treatment of an intracellular pathogen.

Further aspects of the present invention are directed to a method for treating or for preventing a pathogen infection by administering the pharmaceutical compositions of the present invention to a patient in need thereof.

The peptide vaccine of the invention is administered in an immunogenically effective amount with or without a co-stimulatory molecule. According to the method of the invention, the peptide vaccine may be administrated to a subject in need of such treatment for a time and under condition sufficient to prevent, and/or ameliorate the pathogen infection.

The peptide of the invention may be used in conjunction with a co-stimulatory molecule. Both molecules may be formulated separately or as a "chimeric vaccine" formulation, with a pharmaceutically acceptable carrier and administered in an amount sufficient to elicit a T lymphocyte-mediated immune response.

According to the methods of the invention, the peptide may be administered to subjects by a variety of administration modes, including by intradermal, intramuscular, subcutaneous, intravenous, intra-atrial, intra-articular, intraperitoneal, parenteral, oral, rectal, intranasal, intrapulmonary, and transdermal delivery, or topically to the eyes, ears, skin or mucous membranes. Alternatively, the antigen may be administered ex-vivo by direct exposure to cells, tissues or organs originating from a subject (Autologous) or other subject (Allogeneic), optionally in a biologically suitable, liquid or solid carrier.

In certain embodiments of the invention, the peptides or pharmaceutical compositions with or without a co-stimulatory molecule are delivered to a common or adjacent target site in the subject, for example to a specific target tissue or cell population in which the vaccine formulation is intended to elicit an immune response. Typically, when the peptide or pharmaceutical composition and the optional co-stimulatory molecule are administered separately, they are delivered to the same or closely proximate site(s), for example to a single target tissue or to adjacent sites that are structurally or fluidly connected with one another (e.g., to allow direct exposure of the same cells, e.g., fluid flow transfer, dissipation or diffusion through a fluid or extracellular matrix of both vaccine agents). Thus, a shared target site for delivery of antigen and co-stimulatory molecule can be a common surface (e.g., a mucosal, basal or lunenal surface) of a particular target tissue or cell population, or an extracellular space, lumen, cavity, or structure that borders, surrounds or infiltrates the target tissue or cell population.

For prophylactic and treatment purposes, the peptide vaccine with or without a co-stimulatory molecule may be administered to the subject separately or together, in a single bolus delivery, via continuous delivery (e.g., continuous intravenous or transdermal delivery) over an extended time period, or in a repeated administration protocol (e.g., on an hourly, daily or weekly basis). The various dosages and delivery protocols contemplated for administration of peptide and co-stimulatory molecule, in simultaneous or sequential combination, are immunogenically effective to prevent, inhibit the occurrence or alleviate one or more symptoms of infection in the subject. An "immunogenically effective amount" of the peptide thus refers to an amount that is, in combination, effective, at dosages and for periods of time necessary, to elicit a specific T lymphocyte mediated immune response. This response can be determined by conventional assays for T-cell activation, including but not limited to assays to detect proliferation, specific cytokine activation and/or cytolytic activity, as demonstrated in the Examples below.

For prophylactic and therapeutic use, peptide antigens might be formulated with a "pharmaceutical acceptable carrier". As used herein, "pharmaceutically acceptable carrier" includes any and all solvents, dispersion media, coatings, antibacterial and antifungal agents, isotonic and absorption enhancing or delaying agents, and other excipients or additives that are physiologically compatible. In specific embodiments, the carrier is suitable for intranasal, intravenous, intramuscular, intradermal, subcutaneous, parenteral, oral, transmucosal or transdermal administration. Depending on the route of administration, the active compound may be coated in a material to protect the compound from the action of acids and other natural conditions which may inactivate the compound.

Peptide or polypeptide vaccines may be administered to the subject per se or in combination with an appropriate auxiliary agent or adjuvant via injection. Alternatively, the peptide or polypeptide vaccine may be percutaneously administered through mucous membrane by, for instance, spraying the solution. The unit dose of the peptide typically ranges from about 0.01 mg to 100 mg, more typically between about 100 micrograms to about 5 mg, which may be administered, one time or repeatedly, to a patient.

Examples of auxiliary agents or adjuvants which can be formulated with or conjugated to peptide or protein antigens and/or vectors for expressing co-stimulatory molecules to enhance their immunogenicity for use within the invention include cytokines (e.g. GM-CSF), bacterial cell components such as BCG bacterial cell components, immunostimulating complex (ISCOM), extracted from the tree bark called QuillA, QS-21, a saponin-type auxiliary agent, Montanide ISA 51VG, liposomes, aluminum hydroxide (alum), bovine serum albumin (BSA), tetanus toxoid (TT), keyhole limpet hemocyanin (KLH), and TLR (Toll-like receptor)-based adjuvants (e.g. see Heit at al Eur. J. Immunol. (2007) 37:2063-2074).

In preparing pharmaceutical compositions of the present invention, it may be desirable to modify the peptide antigen, or to combine or conjugate the peptide with other agents, to alter pharmacokinetics and biodistribution. A number of methods for altering pharmacokinetics and biodistribution are known to persons of ordinary skill in the art. Examples of such methods include protection of the proteins, protein complexes and polynucleotides in vesicles composed of other proteins, lipids (for example, liposomes), carbohydrates, or synthetic polymers. For example, the vaccine agents of the invention can be incorporated into liposomes in order to enhance pharmacokinetics and biodistribution characteristics. A variety of methods are available for preparing liposomes, as described in, e.g., U.S. Pat. Nos. 4,235,871, 4,501,728 and 4,837,028. For use with liposome delivery vehicles, peptides are typically entrapped within the liposome, or lipid vesicle, or are bound to the outside of the vesicle.

Within certain embodiments of the invention, peptide antigens are associated with liposomes, such as lecithin liposomes or other liposomes known in the art, as a DNA-liposome mixture, or the DNA may be associated with an adjuvant known in the art to boost immune responses, such as a protein or other carrier. Additional agents which assist in the cellular uptake of DNA, such as, but not limited to, calcium ions, viral proteins and other transfection facilitating agents and methods may also be used to advantage.

EXAMPLES

Measurement of Proliferation Responses Induced by VXL Tuberculosis Vaccine Candidates (VC)

Figure 2B:
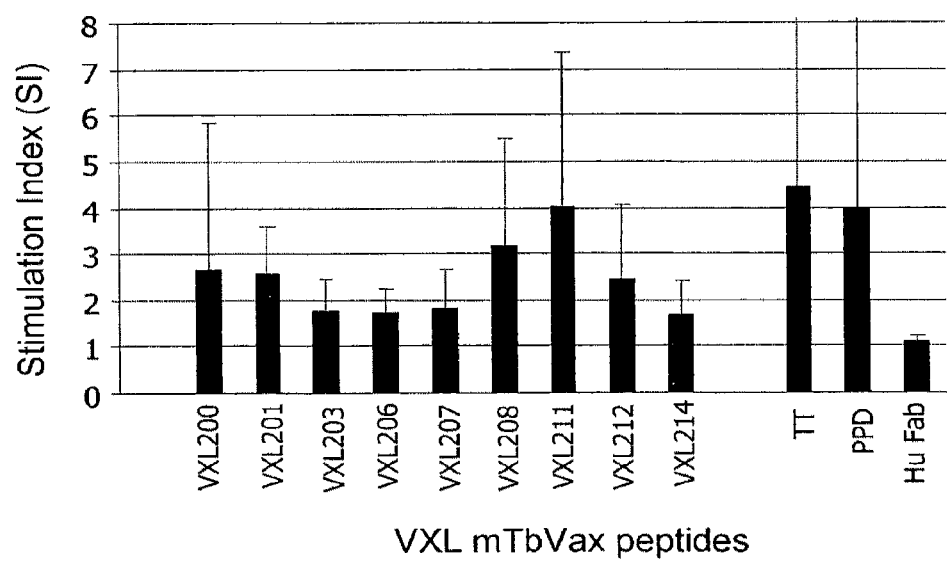

Peripheral blood mononuclear cells (PBMC) from 11 naïve human donors were individually stimulated with 10 µg/ml of partially purified (>70%), VXL tuberculosis VCs for 6 days. On day 6, 0.5 µCi/well of $^3$[H] Thymidine was added for an additional incubation of 18 hours. Samples were harvested and the radioactive counts were measured in a β-counter. The list of VXL VCs is presented in FIG. 1. The controls used in this study were phytohaemagglutinin (PHA), tuberculosis purified protein derivative (PPD) and tetanus toxoid (TT) for positive stimulation and Hu-Fab fragment as a negative stimulation (Morgan EL and Weigle WO (1981) J Exp Med: 154778-790). Results presented in FIG. 2 are indicated as positive stimulation index SI≥2 (A) or as an average SI (B) from an average of 8 different experiments using 11 naïve donors. SI was calculated by dividing the CPM obtained in an analyzed sample to the CPM in control medium sample. Results revealed strong SI of 2.6+/−1 to 4+/−3.3 for VXL201, VXL203, VXL208, VXL211 and VXL212 (FIG. 2B) with positive (SI≥2) proliferation to these peptides in 54%-81% of the donors. The results were statistically significant as measured in a T-Test analysis (p<0.05 or lower) for all the vaccine candidates tested, except for VXL200 (FIG. 2A) as compared to the Hu-Fab negative control. Conclusion: VCs VXL 201, 208, 211, 212 and to some extent also 203 showed the highest SI and widest coverage in the total 11 donors evaluated, in comparison with the positive controls. The results support the pan MHC coverage of the VXL VCs of the invention.

Figure 3A:
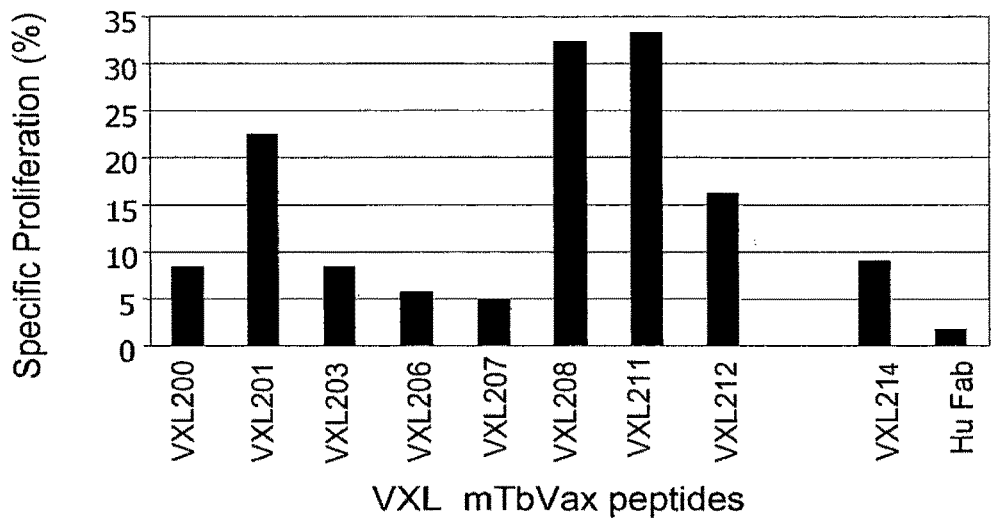
FIG. 3 is a graphical representation of proliferation responses induced by VXL tuberculosis vaccine candidates on TT or PPD positive naïve PBMC. The graph presents the % of positive >2 proliferation in response to the vaccine candidates (VC) in PBMC derived only from donors which are also positive (>2) for the TT antigen (A) or the TB antigen PPD (B). In this experiment TT or PPD were considered as 100% positive. Results are an average of 5 (A) and 4 (B) different experiments.
Figure 3B:
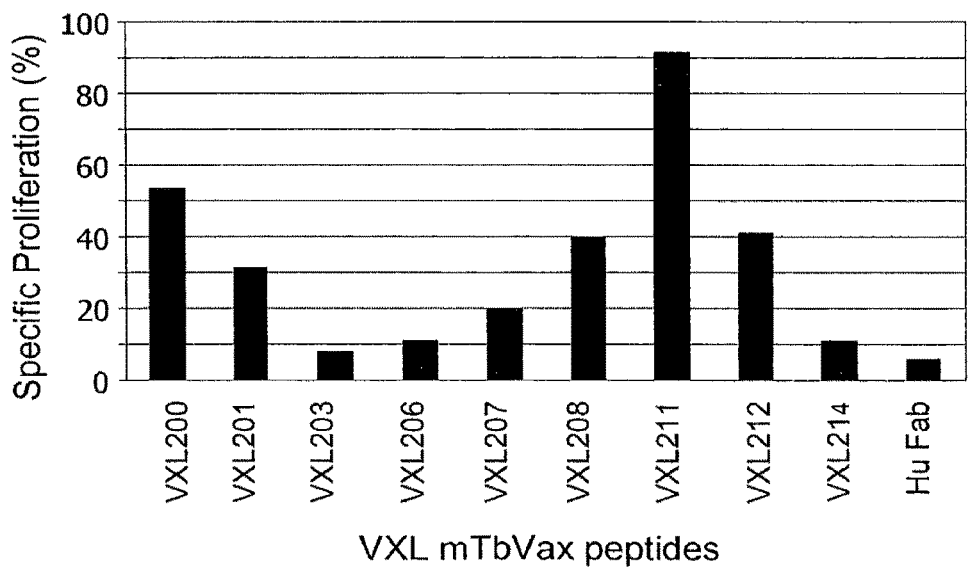

FIG. 3 represents an experiment in which the proliferative properties of the VXL tuberculosis vaccine candidates shown in FIG. 2 were further analyzed only on Tetanus Toxoid (TT) or Tuberculosis Purified protein derivative (PPD) positive responded (SI≥2) naïve PBMC. Namely, on PBMC obtained from donors previously exposed to the tuberculosis bacteria or vaccinated against the tetanus antigen or tuberculosis. The experiment was performed as described above. Conclusion: The VCs VXL 200, 201, 208, 211, 212 are stronger in healthy donors which also manifested response to PPD i.e. they are potentially more associated with anti-tuberculosis immunity. In parallel, VCs VXL 201, 208, 211, 212 and to some extent also 214, 200 and 203 are more positive in donors, which also manifested response (SI≥2) to TT i.e. they are active in an immunocompetent system.

Figures 4A, 4B:
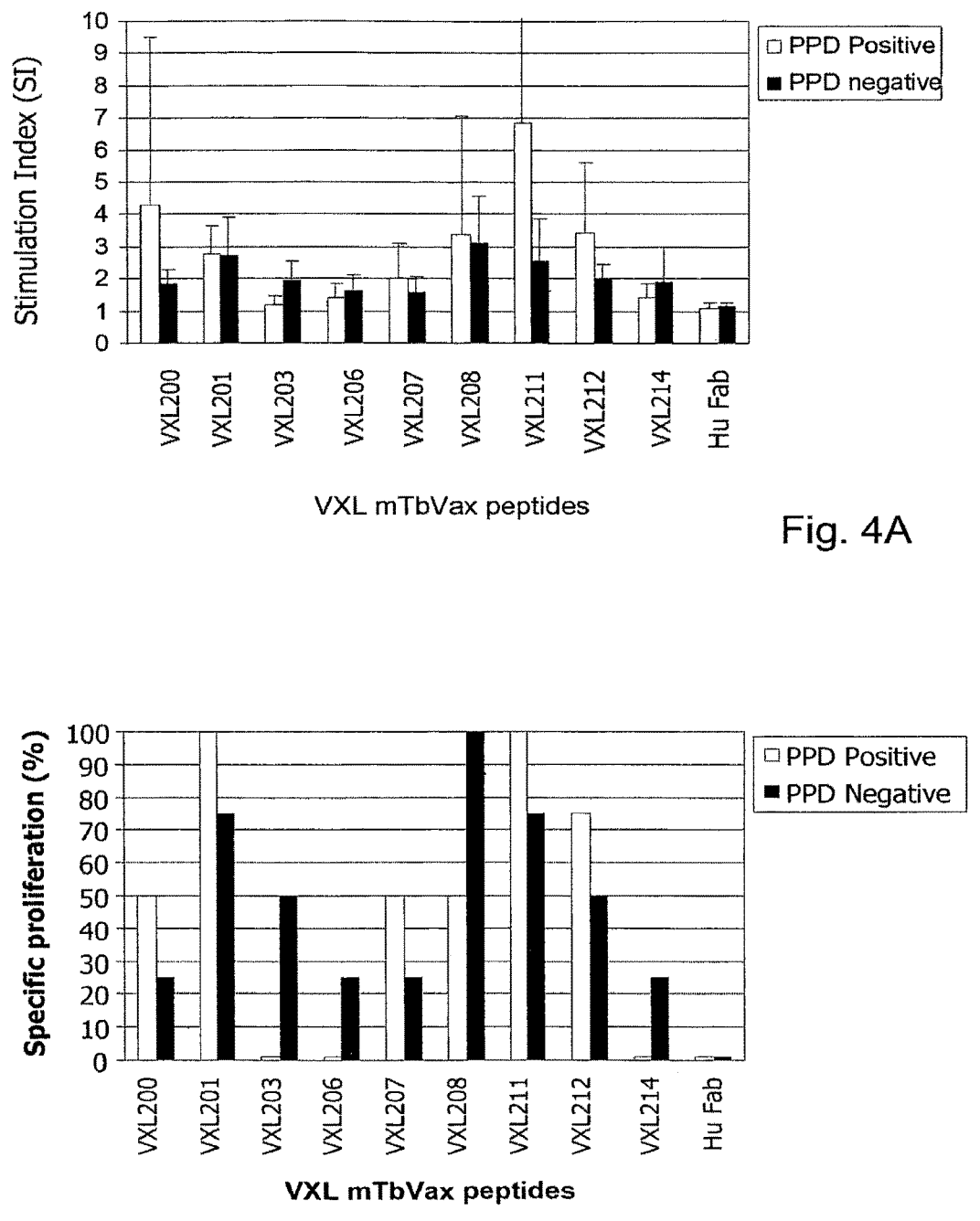

FIG. 4 represents an experiment in which the proliferative properties of the VXL tuberculosis vaccine candidates shown in FIG. 2 was further analyzed only on naïve PBMC derived from PPD positive versus PPD negative donors. The experiment was performed as described above. Conclusion: VCs VXL 201, 208, 211, 212 are stronger antigens in naïve donors and are even stronger in donors with previous exposure to the tuberculosis Bactria. VXL 203 is more potent in donors which were not exposed in the past to the tuberculosis Bactria. There is a role for both types of antigens in the development of preventive vs. therapeutic vaccine.

Figure 6A:
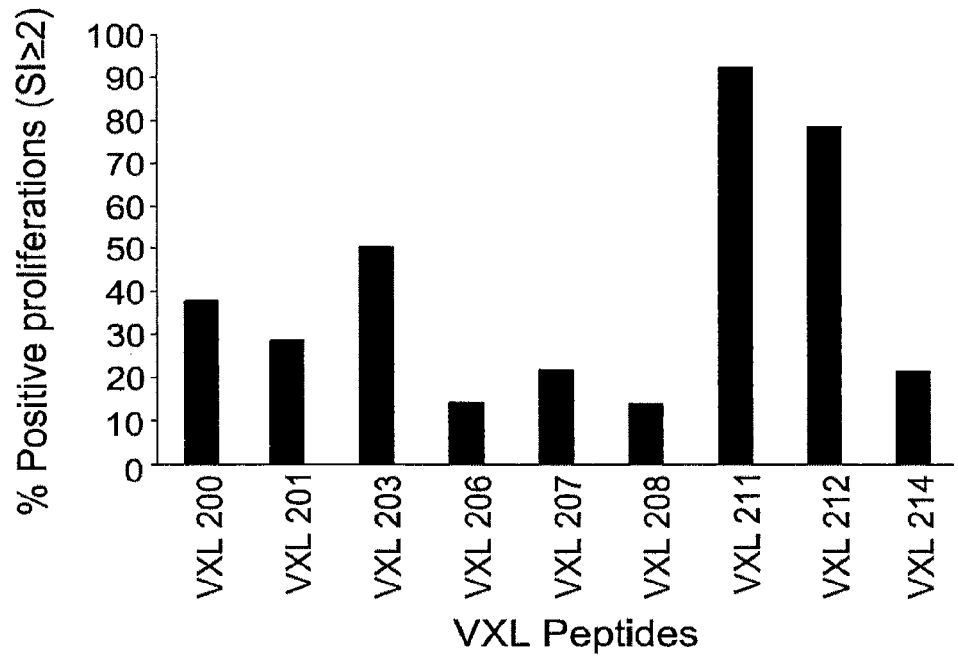
FIG. 6 is a graphical representation of proliferation responses of PBMC obtained from patients with active Mtb in response to stimulation in vitro with various Mtb peptides of the invention (designated VXL peptides). Results are indicated as a positive stimulation index SI≥2 (A) or as an average stimulation index (SI) and standard deviation (SD) (B) and represent an average of 4 different experiments using 14 TB patients.
Figure 6B:
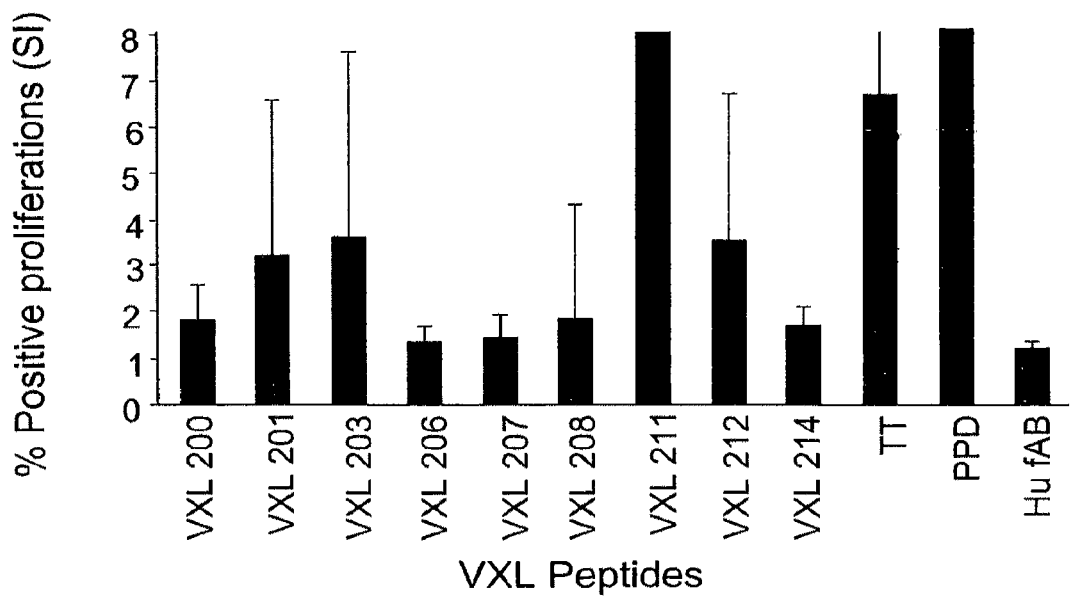

We next conducted similar proliferation studies with peripheral blood mononuclear cells (PBMC) from 14 patients with active Mtb. The characterization of these tuberculosis patients and in particular their ethnic group and disease-associated parameters are described in FIG. 5. Similar to other proliferation studies, controls used in this study were PHA, PPD and TT for positive stimulation and Hu-Fab as a negative stimulation. Proliferation results presented in FIG. 6 are indicated as positive stimulation index SI≥2 (A) or as an average SI (B) from an average of 4 different experiments using 14 TB patients. Results revealed extremely strong SI of 3.2+/−3.4 to 8.0+/−6.8 for VXL201, VXL203, VXL211 and VXL212 with positive (SI>2) in 54-100% of the patients evaluated. The proliferation in TB patients was significantly stronger compared to that in naïve donors suggesting a primary recognition/priming against the VXL VCs by the patient's immune system. The results were statistically significant (T-Test p<0.05 or lower) for all the vaccine candidates (excluding VXL208) tested as compared to the Hu-Fab negative control. In addition results are also significant (T test p<0.05 or lower) for the vaccines candidate VXL201, VXL203, VXL211, VXL212 as compared to the other vaccine candidates.

Measurement of Cytokine Secretion Responses Induced by VXL Tuberculosis Vaccine Candidates (VCs)

Figure 7A:
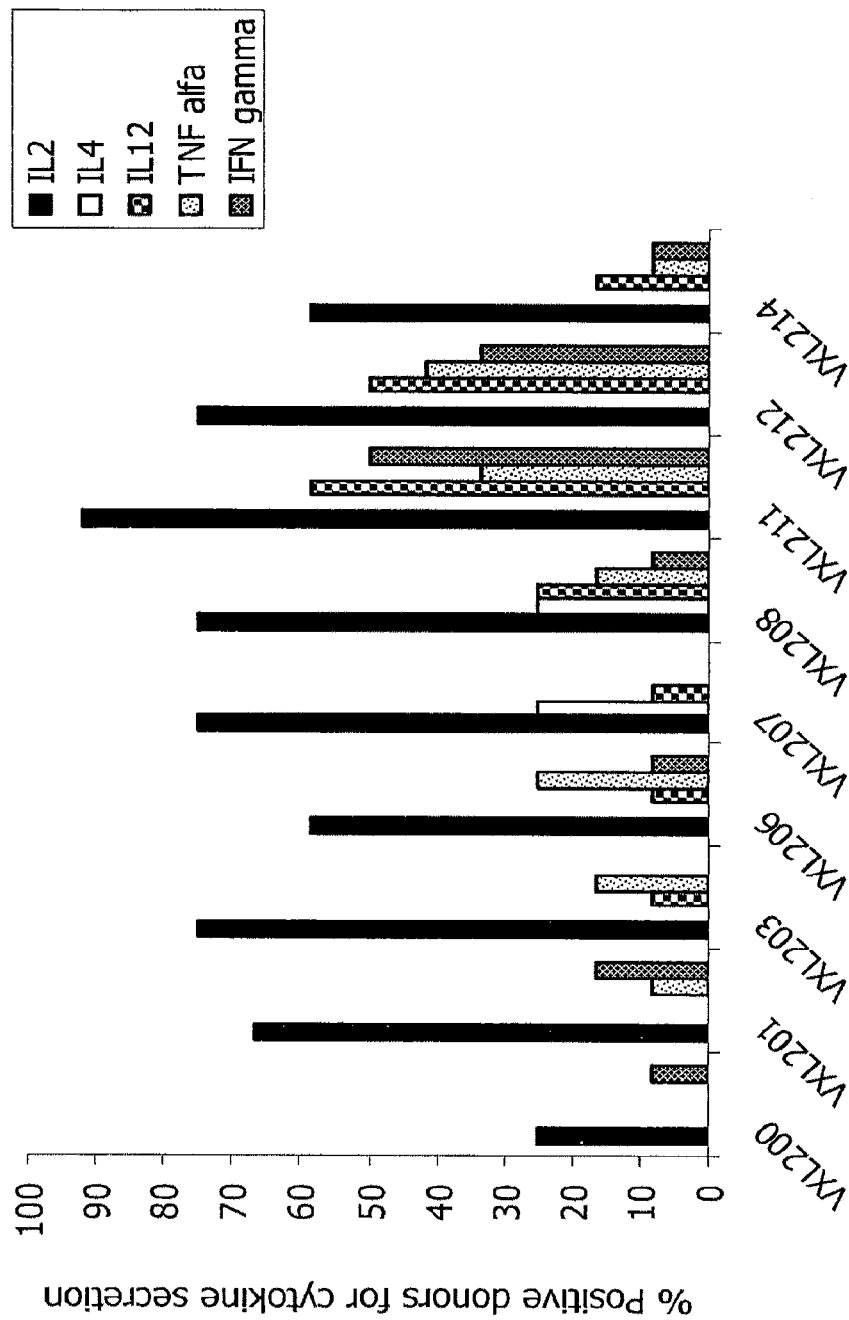
FIG. 7A represents the percentage of donors with positive (x>0.1 ng/ml) cytokine secretion from the 11 evaluated naïve donors, upon stimulation with various peptides of the invention.

In order to define the Th1 or Th2 profile during the stimulation process with the different VXL VC, PBMC derived from 11 naïve donors were individually stimulated once by all the partially purified (>70% pure) tuberculosis VCs for 48 hrs and supernatant was used to evaluate cytokine levels in a quantitative ELISA assay. Results in FIG. 7A present the percentage of donors with positive (x>0.1 ng/ml) cytokine secretion from the 11 evaluated naïve donors. FIG. 7B presents one of three similar experiments for cytokine secretion and proliferation response to VXL203, VXL208, VXL211, VXL212 using 5 of the 11 donors. Results in FIG. 7A shows that IL-2 secretion is observed following stimulation with each of the VXL VCs but widely ranged from 25% of the donors with VXL200 to 91.6% with VXL211. IL-4 secretion was much lower and observed only following stimulation with VC VXL 207 and 208 in 25% of the donors. IL-12 secretion levels ranged from 8.6% with VXL203, 206, 207 to 58.3% in VXL 211 and VXL212. IFN-gamma and TNF alfa secretion levels ranged from 8.6-50% and 8.6-41.6% with the same VCs. These results indicate that the best VCs for inducing Th1 immunity in these donors were VXL211 and VXL212 and to some extent also VXL 201, VXL203 and VXL208. In the second experiment, FIG. 7B, the cytokine secretion analysis showed a broad secretion (1.5-3.3 ng/ml) of IL-2, IL-12, TNF-alfa, IFN-gamma and to a lesser extent IL-4 by the VXL203, VXL208, VXL211, VXL212 VCs. In these donors, the high secretion levels were correlated with strong SI.

Figure 8A:
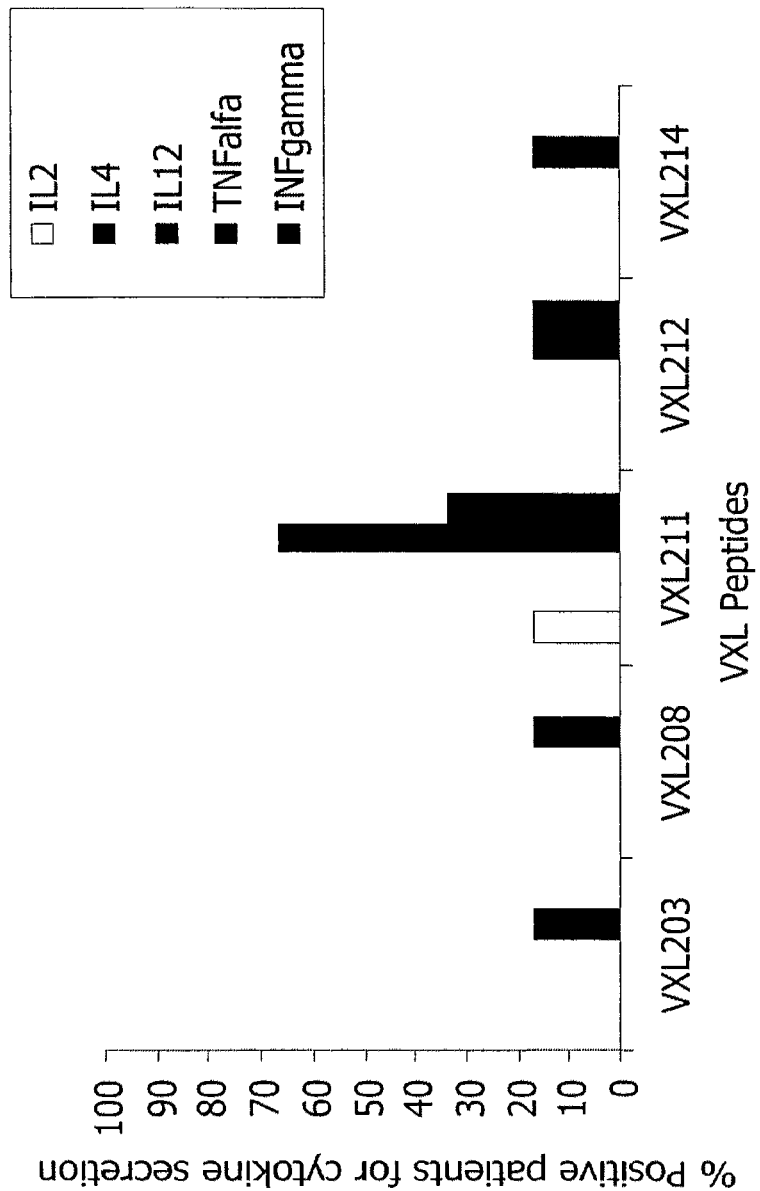
FIG. 8A represents the percentage of donors with positive (X>0.1 ng/ml) cytokine secretion from the 6 evaluated donors with active TB, upon stimulation with various peptides of the invention.

FIG. 8A, B presents similar experiments conducted with PBMCs derived from 6 tuberculosis patients. Results in FIG. 8A present a low percentage of positive (x>0.1 ng/ml) cytokine secretion from the 6 evaluated donors with active TB. Results in FIG. 8B revealed lower (1.12-1.89 ng/ml) secretion which was limited mainly to TNF-alfa and IFN-gamma by VCs VXL211 and VXL212. In addition, unlike in naïve donors in these patients there was no correlation between the low levels and the strong SI values. Conclusion: In naïve donors, VXL203, VXL208, VXL211, VXL212 and to some extent VXL201 were the most potent VCs in inducing high secretion of IL-2, IL-12 and/or IFN-gamma which are key Th1 cytokines associated with anti-TB immunity. Among these VCs only VXL208 induced some secretion of IL-4 which can lead to a mix Th1 and Th2 immunity combining T cells and antibodies. In these studies, specific cytokine secretion was mostly correlated with high SI in proliferation analysis in the majority of the evaluated donors. On the contrary, high SI scores in patients with active tuberculosis were usually associated with lower secretion levels of mainly IL-12 and IFN-gamma and were observed only in few of the donors. As already shown by (Tones M et al., 1998) this phenomenon represents the poor immune status of these patients and inhibition of immunological function of peripheral lymphocytes by the *M. Tuberculosis* (Dietrich J. et al 2009) and set a higher bar for any future anti-TB therapeutic vaccine.

Figure 9A:
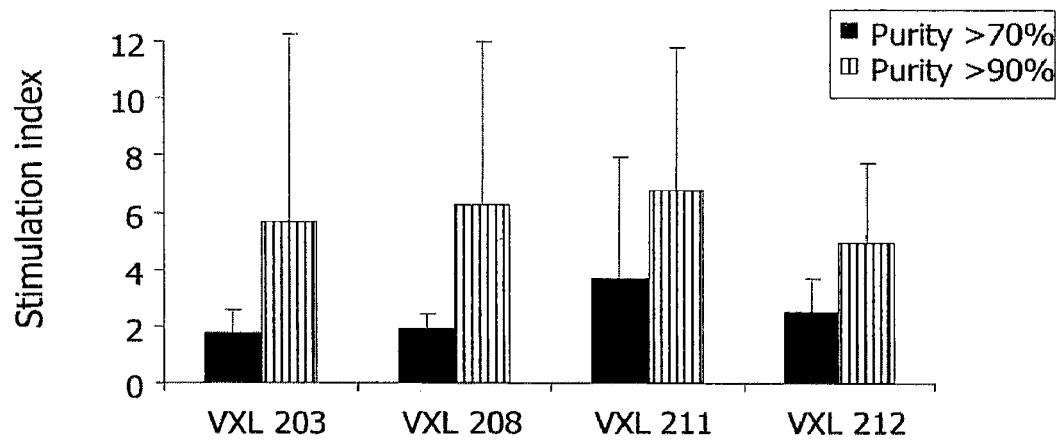
FIG. 9 is a graphical representation of proliferation responses of PBMC obtained from naïve donors (FIG. 9A) and Mtb patients (FIG. 9B) in response to stimulation in vitro with various Mtb peptides of the invention. Two types of peptides were used in the experiment: peptides having purity of more than 70% and peptides having purity of more than 90%. The results are presented as stimulation index (SI).
Figure 9B:
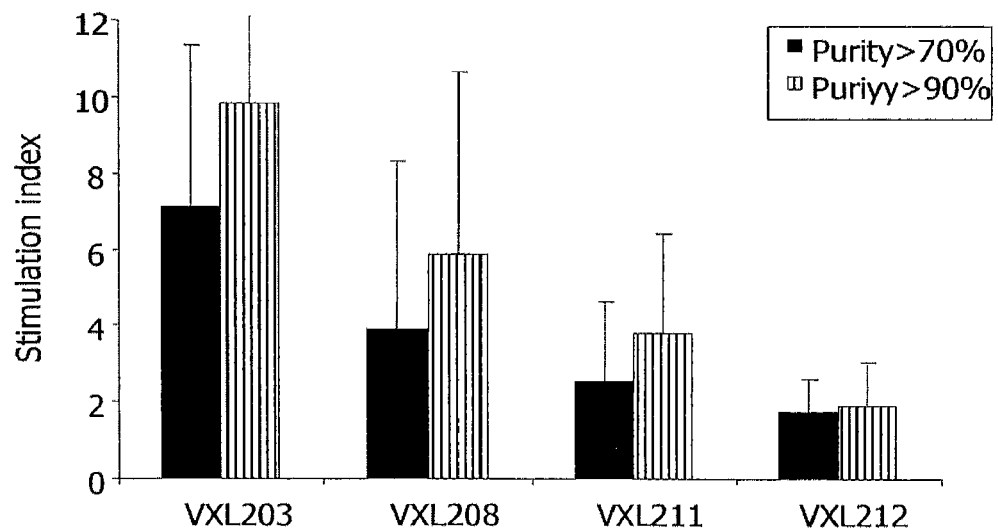

Based on the above described initial proliferation and cytokine secretion experiments, the VCs VXL 201, 203, 208, 211 and 212 were selected for further evaluation. These multi-epitope peptides were re-synthesized, further purified (purity>90%) and revalidated in 2 proliferation experiments for bioactivity/specificity in comparison to the same semi-purified (>70% pure) peptides. Experiments were conducted as previously described on six additional healthy naïve donors and 4 TB patients. The results shown in FIG. 9 present higher SI scores for the pure VCs in naïve donors (FIG. 9A) and TB patients (FIG. 9A). Among the different VCs a significant elevation in proliferation potency was manifested mainly by VXL203 with average SI levels of 1.8+/−0.8 in the partially purified peptide compared with 5.7+/−6.8 for pure peptide on naïve donors. Moderate elevation was also observed in proliferation studies performed in PBMC derived from TB patients PBMC FIG. 9B. Conclusion: Results confirmed the potency and specificity of the selected immunodominant VCs in naïve individuals and in TB patients.

Figure 10:
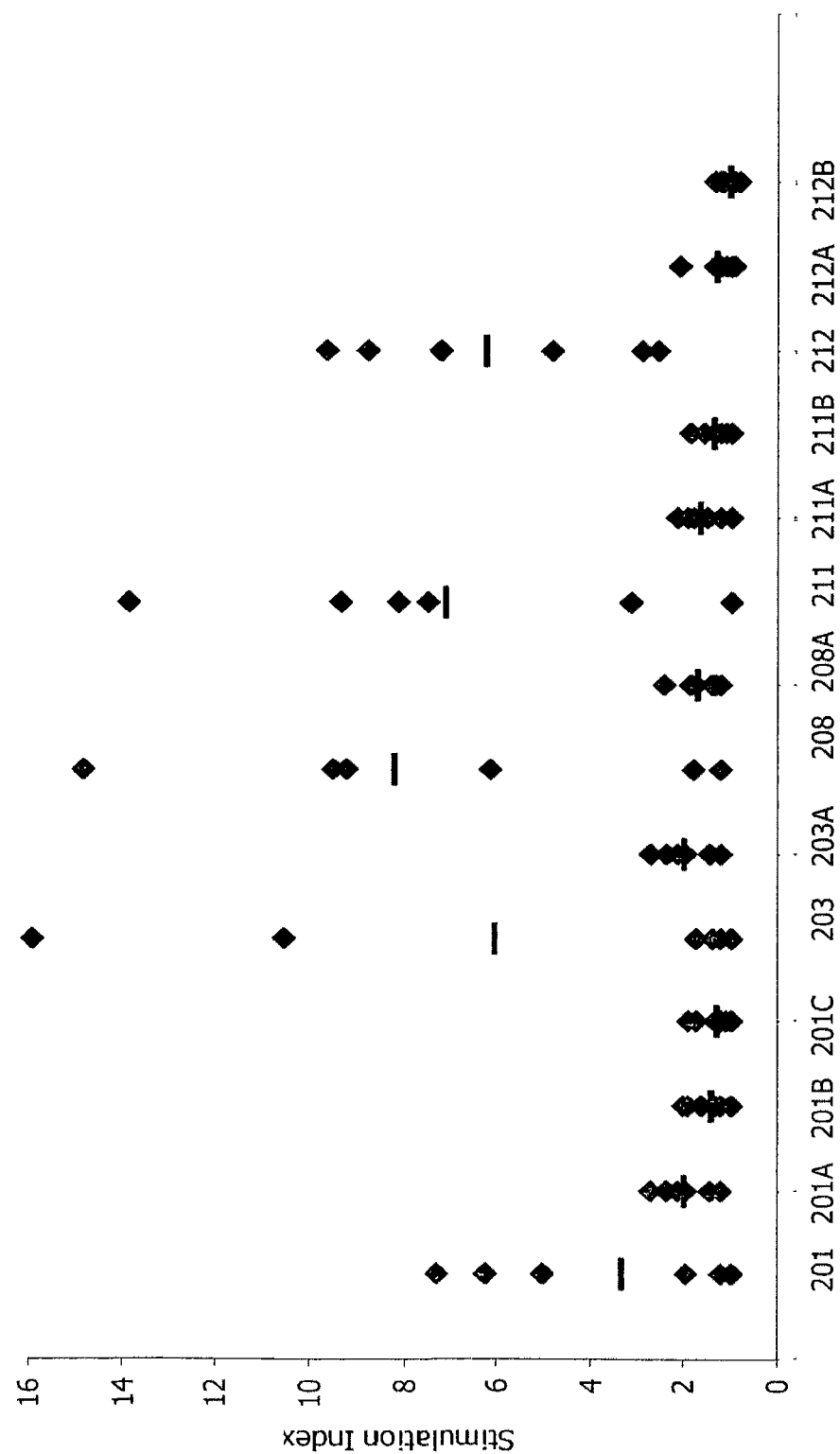
FIG. 10 is a graphical representation of proliferation responses of PBMC obtained from naïve donors in response to stimulation in vitro with various Mtb peptides of the invention as compared with other known or novel epitopes derived from the same tuberculosis antigens (control peptides). The results are presented as stimulation index (SI).
Figure 11A:
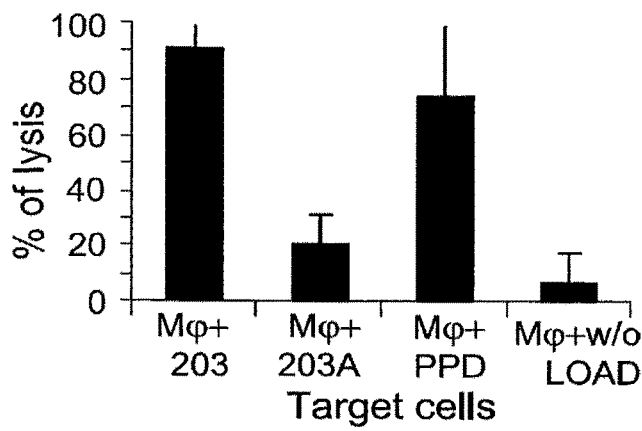
FIG. 11 is a graphical representation of cytotoxic activity of T cell lines generated against the peptides of the invention: Anti VXL 203 CTL (FIG. 11A), Anti VXL 208 CTL (FIG. 11B), Anti VXL 211 CTL (FIG. 11C), and Anti VXL 212 CTL (FIG. 11D). Results are presented as percent lysis of target cells, macrophages (Mφ) pre-loaded with the respective VXL peptide. Macrophages loaded with control antigen match, or PPD, or unloaded macrophages served as controls.
Figure 11B:
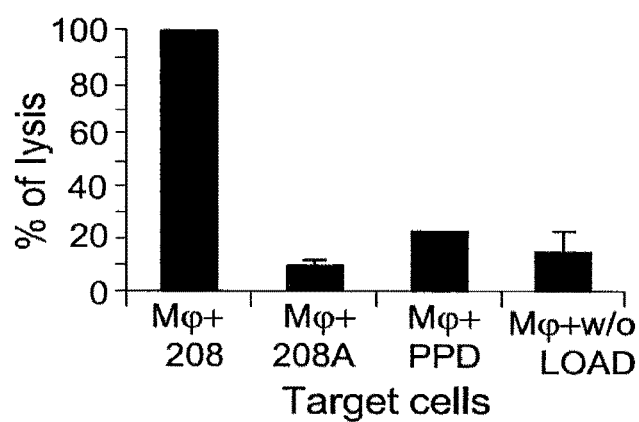
Figure 11C:
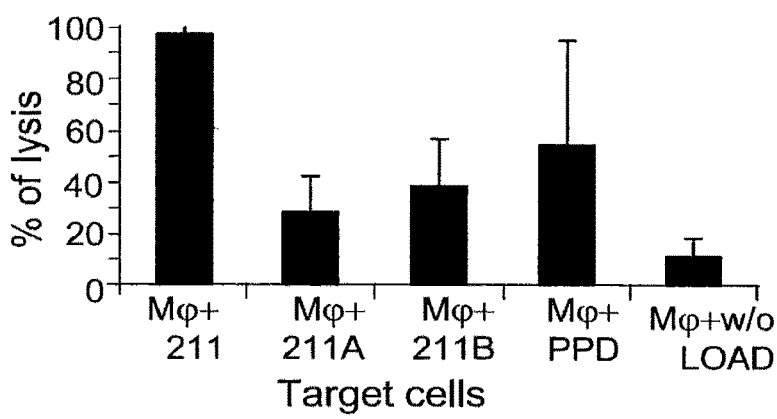
Figure 11D:
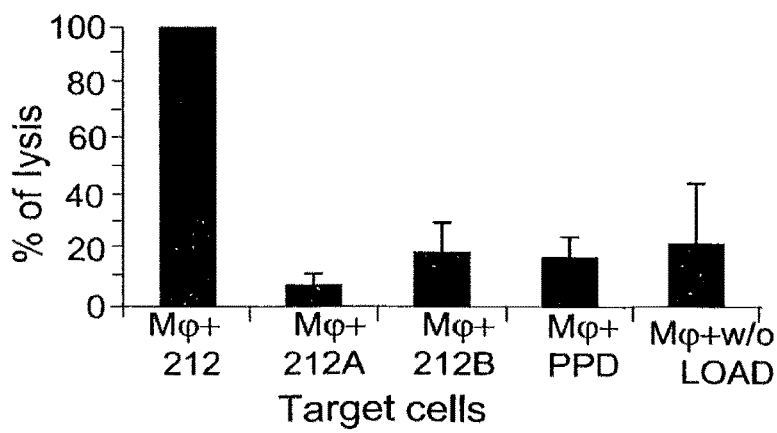

To further confirm the superior immunogenic properties of the Signal Peptide derived multi-epitope peptides VXL201, VXL203, VXL208, VXL211, VXL212, their proliferation properties were compared with control peptides derived from other domains in the same antigens. FIG. 10 represents one of two similar experiments in which the proliferative effect of VXL tuberculosis VCs was compared to that of other known or novel epitopes derived from the same tuberculosis antigens. PBMCs from 6 naïve donors were individually stimulated for 6 days by crude VXL201 (>70% purity) and pure (>90% purity) VXL203, VXL208, VXL211, VXL212 or alternative known and novel pure (>90% purity) peptide epitopes derived from the same antigens. The alternative non SP-derived peptide epitopes were selected and scored according to their predicted MHC binding as follows: A—high, B-medium, or C-Low MHC class I binding. The length of previously published alternative epitopes was kept as is; while the length of novel alternative epitopes was adjusted to that of the evaluated antigen matched VXL VCs. Results suggested that proliferation is significantly higher with all VXL VC vs. their alternative antigen-match control VCs. While VXL VCs manifested absolute average SI score ranging from 4-7, each alternative VCs excluding VXL201A manifested negative SI≤2. These results are highly significant (T-Test p<0.01 or lower) for any VXL VC vs. its alternative antigen-match VC excluding VXL201 vs. 201A (P=0.077). One potential explanation for the results obtained with VXL201 VC could be related to its final purity (70% vs. 90% for other peptides). Comparable results were achieved in a similar analysis conducted with TB patients (data not shown). Conclusions: The SP-derived multi-epitope VCs VXL 201, VXL203, VXL208, VXL211, VXL212 are far more immunodominant than any other known or novel epitope selected from a different domain on the same tuberculosis antigen. Moreover, these results show that the ability of inducing immunity in heterogeneous population of naïve or TB patients-derived PBMC is mostly restricted to SP-derived VCs.

Next, an in depth analysis of the phenotype and function of T cell lines generated against the five selected VCs was performed. T-cell lines were generated against the five individual VXL VCs as follows: 3 naïve donors against VXL203, 2 naïve donors against VXL208, 3 naïve donors VXL211, 2 naïve donors against VXL212 and one patient against VXL211. T cell generation was performed by initial stimulation of PBLs with VC-pulsed autologous DC, followed by stimulation with autologous peptide-loaded macrophages and a final stimulation with soluble VC. The established T-cell lines were then evaluated for their cytotoxic activity. Autologous Macrophages were loaded for 18 hrs with 50 µg/ml VXL VCs, Control antigen match VCs, or PPD, labeled for 14 hours with 35S Methionine and used as targets. An additional control used was non-loaded Macrophages. FIG. 11 presents an average cytotoxic activity in three different experiments using 2 or 3 different donors. Cytotoxicity at 50:1 E:T ratio by VXL203, 208, 211 and 212-induced T cells against the same evaluated VXL VC (peptide) was very strong and highly specific at the range of 90-100% lysis vs. 5-30% of the different controls including the alternative antigen-match non-SP peptides and unloaded targets. T cell lines induced against VXL203 and VXL211 also manifested specific lysis against PPD-loaded DC suggesting the presence of VXL203 and VXL211 in the PPD's antigenic repertoire. Results are highly significant (T-Test $p<0.01$ or lower) for each VXL VC vs. its alternative antigen-match epitopes A or B and PPD excluding VXL203 and VXL211 vs. PPD.

Next, the lysis properties of the same peptide-induced T cell lines against autologous macrophages (Mφ) infected with live Mtb was evaluated. Mφ were infected for 18 h with live bacteria at a ratio of 1:10 Mφ:bacteria in RPMI complete Medium without antibiotics. Next, the medium was removed and the Mφ were further incubated for additional 48 h in RPMI complete medium with the G418 antibiotic which specifically inhibits the extracellular growth of the Mtb bacteria. For the cytotoxicity assay infected Mφ (target cells) were washed and cultivated at a ratio of 1:100 and/or 1:50 with VXL-induced T cell lines (effectors) for 5 h. At the final step, the bacteria growth medium was collected, separated from cells, washed, diluted 1:1000 in RPMI medium and 1 ml was used to seed the bacteria on dedicated dishes with Middlebrool 7H9 solid medium. For evaluating the spontaneous lysis, infected Mφ were incubated with complete RPMI medium containing an equal number of non stimulated PBMCs from donors or patients. For total lysis, infected mφ were treated with 1 ml of 10% Tryton X100. Dishes were incubated in 37° C. for 2 weeks and colony forming units (CFU) were counted. The percentage of specific lysis was calculated as follows: No. of colonies in Exp. dish (-) No. of colonies in spontaneous dish (/) No. of colonies in Total dish (-) No. of colonies in spontaneous dish.

Figure 12A:
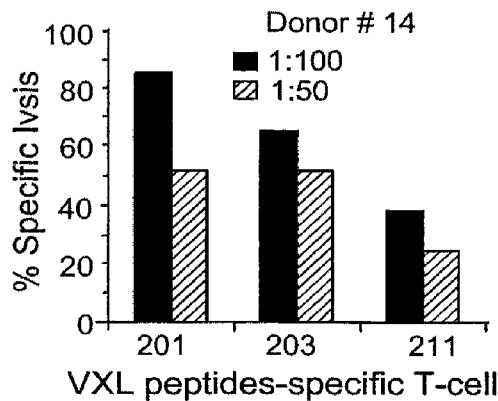
FIGS. 12A and 12B—represent data obtained with naive donor-derived T cell lines and FIGS. 12C, 12D and 12E—represent data obtained with Mtb patients-derived T cell lines.

FIGS. 12A and B summarize the cytotoxicity properties of the naive and patient-derived T-cell lines. The results suggest high and specific lysis by anti-VXL201 and anti-VXL203 and moderate lysis by anti VXL211 T cell lines in both naïve and TB patients. Anti-VXL208 and VXL212 T cell line manifested lower lysis levels in these studies. FIG. 13A, B summarizes the positive VCs-specific donor and patient T cells as well as their range of activity in the cytotoxicity assay. As an additional parameter for potency, levels of the Th1 cytokine IFN-gamma released by the anti-VXL201, 203, 211 effector T-cells lines during the lysis process, were measured in an ELISA assay. Very significant levels of IFN-gamma secretion by both naïve and TB-patient-derived T cell lines in particular anti-VXL201 and anti-VXL203 were detected, as follows:

For donor #14 (FIG. 12A): upon stimulation with VXL201, 6 µg/ml IFN-gamma were detected; upon stimulation with VXL203, 16 µg/ml IFN-gamma were detected and upon stimulation with VXL211, 9.2 µg/ml IFN-gamma were detected.

Figure 12B:
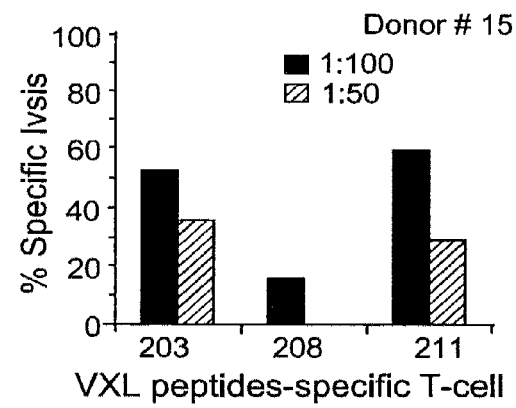

For donor #15 (FIG. 12B): upon stimulation with VXL203, 3.8 µg/ml IFN-gamma were detected; upon stimulation with VXL208, 3.6 µg/ml IFN-gamma were detected and upon stimulation with VXL211, 5.9 µg/ml IFN-gamma were detected.

Figure 12C:
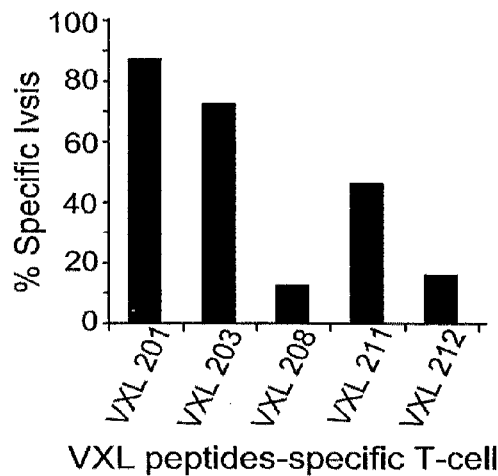
FIG. 12 is a graphical representation of lysis of Mtb infected macrophages by various VXL-peptide induced T cell lines.

For patient #17 (FIG. 12C): upon stimulation with VXL201, 10 µg/ml IFN-gamma were detected; upon stimulation with VXL203, 12 µg/ml IFN-gamma were detected, upon stimulation with VXL208, 2.6 µg/ml IFN-gamma were detected, upon stimulation with VXL211, 7.8 µg/ml IFN-gamma were detected, and upon stimulation with VXL212, 5.6 µg/ml IFN-gamma were detected.

Figure 12D:
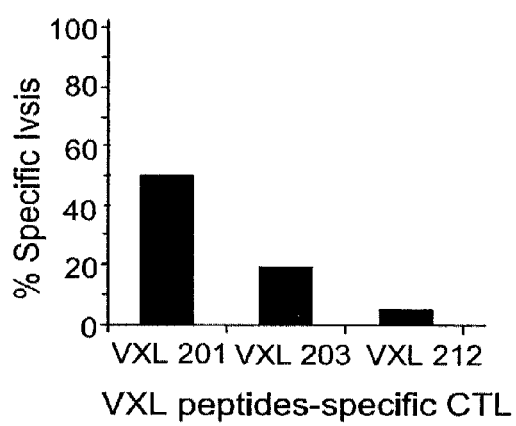

For patient #18 (FIG. 12D): upon stimulation with VXL201, 14 µg/ml IFN-gamma were detected; upon stimulation with VXL203, 11 µg/ml IFN-gamma were detected, and upon stimulation with VXL212, 7.5 µg/ml IFN-gamma were detected.

Figure 12E:
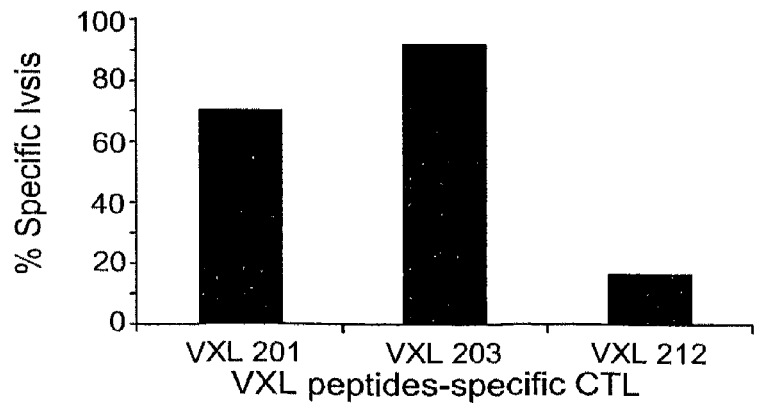

For patient #19 (FIG. 12E): upon stimulation with VXL201, 11.3 µg/ml IFN-gamma were detected; upon stimulation with VXL203, 4.6 µg/ml IFN-gamma were detected, and upon stimulation with VXL212, 3.6 µg/ml IFN-gamma were detected.

This intensive secretion was correlated with the high specific lysis of these T cell lines. Conclusions: The five selected VXL VCs in particular VXL 201, 203, 211 are potent inducers of IFN-gamma secretion from T cell lines with specific and robust lysis capability of both peptide-loaded and bacteria infected targets. Moreover, cytotoxicity results confirmed the processing and presentation of the VXL peptides on the surface of target cells. More importantly, the effective lysis of T cell lines isolated from tuberculosis patient suggest that the VXL VCs are potent candidates as therapeutic vaccines in addition to serving as a preventive vaccine, i.e. transforming non-responsive PBMC with limited cytokine secretion properties to functional T cells with high lysis and cytokine secretion properties. Last but not least, these results also validate the ability of Mtb antigenic epitopes to be efficiently presented on the host cells in association with MHC molecules, and thereby allow their specific destruction.

The phenotype of the T cell population during development and at the final stage whereby they are used in cytotoxicity studies, were evaluated by FACS analysis.

FIG. 14, presents results of the evaluation of four anti-VXL VCs T cell lines developed from 2 naïve donors. The CD4+ or CD8+ positive T cell population expressing the effector cell marker $CD44^{high}$ and effector memory marker $CD62L^{high}$ was examined.

Results shown in FIG. 14 demonstrate a significant increase in $CD8+/CD44^{high}$ and $CD8+/CD62L^{high}$ subpopulation after the $3^{rd}$ stimulation with each evaluated anti-VXL VCs T-cell line in particular VXL203 and VXL211. The increase in CD44$^{high}$ activated effector cells ranged from 79% to 80% and from 17% to 40.9% in CD62L$^{high}$ memory cells for VXL203 and VXL211 respectively. VXL208 manifested a lower increase in CD44$^{high}$ activated effector cells 50.2% and 32.1% in CD62L$^{high}$. CD4+ T cells demonstrated an increase in CD4+/CD44$^{high}$ and CD4+/CD62L$^{high}$ subpopulation already after the 1$^{st}$ stimulation. This level wasn't augmented following the 2$^{nd}$ and 3$^{rd}$ stimulations. The levels of CD44$^{high}$ activated effector cells ranged from 41% for VXL11 to 52% for VXL208 and from 22% for VXL208 to 39% for VXL 203 in CD62L$^{high}$ memory cells. Without wishing to be bound by theory, an explanation for these results can be related to the initial priming of CD4+ cells mediated by the Mtb.

Next, the percentage of IFN-gamma and IL-4 producing CD4+ and CD8+ T-cells was measured in ICS. For this FACS study the matured anti-VXL201, 203 and 211 T cell lines after the 3$^{rd}$ stimulation, developed from two naïve donors, were used. T cell lines were stimulated for 6 h with autologous mφ loaded with the corresponding VXL peptide or antigen-match peptide as a negative control. For achieving a maximal cytokine production the T cells lines were stimulated with 50 ng/ml PMA and 750 ng/ml Ionomycine.

Results presented in FIG. 15, show high and specific IFN-gamma producing T cells following stimulation with VXL Peptide and none following stimulation with the antigen match control peptides. The maximal percentage of specific IFN-gamma produced by CD8+ T-cells was in anti-VXL211 (10.6%) FIG. 15C and anti-VXL203 (8.2%) FIG. 15A upper left as compared to a lower production by 203A FIG. 15B and 211A FIG. 15D. IFN-gamma production was manifested by both CD4+ and CD8+ subpopulation. The same T cell line didn't manifest any IL-4 secretion following stimulation with VXL Peptide and the antigen match control peptides (data not presented). Conclusions: VXL VCs 201, 203, 208 and 211 induced a robust and antigen-specific immune activation by both T-cells subpopulation CD4+ and CD8+. This response was mediated by CD44$^{high}$ activated effector cells and CD62L$^{high}$ memory cells suggesting T cell differentiation to memory post activation. Further more, these cells demonstrated high functionally for INF-gamma (Th1) but not IL-4 (Th2) production in ICS, lysis of peptide-loaded and MTB infected autolugues mφ and IFN-gamma secretion (during the lysis).

The invention claimed is:

1. An immunogenic composition, comprising:
a recombinant polypeptide comprising at least two peptides, wherein the at least two peptides comprise a first peptide consisting of the amino acid sequence of SEQ ID NO: 12, and one or more additional peptides of no longer than 40 amino acids comprising the amino acid sequence selected from the group consisting of SEQ ID NOs: 2, SEQ ID NO: 4 and SEQ ID NO: 9; and optionally at least one adjuvant.

2. The immunogenic composition according to claim 1, wherein a nucleotide sequence encoding the recombinant polypeptide has at least one restriction enzyme site.

3. The immunogenic composition according to claim 1, wherein the recombinant polypeptide has the amino acid sequence of SEQ ID NO: 55 or an amino acid sequence having at least 85% homology with SEQ ID NO: 55.

4. An isolated antigen-presenting cell preloaded with the recombinant polypeptide according to claim 1.

5. A method of treating a pathogenic infection comprising administering the immunogenic composition according to claim 1 to a subject in need thereof.

6. A method of treating a pathogenic infection comprising administering an enriched T cell population to a subject in need thereof wherein the enriched T cell population is obtained by administering the immunogenic composition of claim 1 to a T cell population in vitro.

7. A method for generating anti-tuberculosis antibodies comprising administering the immunogenic composition of claim 1 to an animal or a human subject.

8. The immunogenic composition according to claim 1, exhibiting, upon administration, a combined activation of both $CD4^+$ and $CD8^+$ T cells.

9. The immunogenic composition according to claim 3, wherein the recombinant polypeptide has an amino acid sequence having at least 90% homology with SEQ ID NO: 55.

10. The immunogenic composition according to claim 3, wherein the recombinant polypeptide has an amino acid sequence having at least 95% homology with SEQ ID NO: 55.

11. The immunogenic composition according to claim 1, wherein said immunogenic composition is configured for co-administration with one or more anti-infective agents.

12. The immunogenic composition of claim 1, wherein one or more of the at least two peptides have a C-terminal amide.

* * * * *